(12) United States Patent
Durden

(10) Patent No.: US 6,777,439 B2
(45) Date of Patent: Aug. 17, 2004

(54) COMPOSITIONS AND METHODS FOR IDENTIFYING AGENTS WHICH MODULATE PTEN FUNCTION AND PI-3 KINASE PATHWAYS

(75) Inventor: Donald L. Durden, Indianapolis, IN (US)

(73) Assignee: Advanced Research & Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/870,379

(22) Filed: May 30, 2001

(65) Prior Publication Data

US 2002/0150954 A1 Oct. 17, 2002

Related U.S. Application Data

(60) Provisional application No. 60/208,437, filed on May 30, 2000, and provisional application No. 60/274,167, filed on Mar. 8, 2001.

(51) Int. Cl.$^7$ ......................... A61K 31/12; A61K 31/40
(52) U.S. Cl. ....................................... 514/456; 514/422
(58) Field of Search ................................. 514/422, 456; 424/184.1, 85.1

(56) References Cited

U.S. PATENT DOCUMENTS 6,020,199 A 2/2000 Monia et al.

OTHER PUBLICATIONS

Shibuya, Cancer Sci. Sep. 2003;94(9):751–6.*
Hu et al (Mar. 2000, Clinical Cancer Research, vol. 6, pp. 880–886).*
Oikawa et al (1996, European Journal of Pharmacology, vol. 318, pp. 93–96).*
Jiang et al (Feb. 15, 2002, PNAS vol. 97, pp. 1749–1753).*
Gura (Science, 1997, 278:1041–1042).*
Jain (Sci. Am., 1994, 271:58–65).*
Curti (Crit. Rev. in Oncology/Hematology, 1993, 14:29–39).*
Hartwell et al (Science, 1997, 278:1064–1068).*
Li, Da–Ming, et al., "PTEN/MMAC1/TEP1 suppresses the tumorigenicity and induces G, cell cycle arrest in human glioblastoma cells"; Proc. Natl. Acad. Sci. USA, 95:15406–15411 (1998).
Li, Liwu, et al., "A Family of Putative Tumor Suppressors Is Structurally and Functionally Conserved in Humans and Yeast"; J. Biological Chemistry, 272: 29403–29406 (1997).
Li, Jing, et al., "PTEN, a Putative Protein Tyrosine Phosphatase Gene Mutated in Human Brain, Breast, and Prostate Cancer"; Science 275: 1943–1947 (1997).
Huang, He, et al., "PTEN affects cell size, cell proliferation and apoptosis during Drosophila eye development"; Development 126: 5365–5372 (1999).
Lee, Jie–Oh, et al., "Crystal Structure of the PTEN Tumor Suppressor: Implications for Its Phosphoinositide Phosphatase Activity and Membrane Association"; Cell, 99: 323–334 (1999).
Sun, Hong, et al., "PTEN modulates cell cycle progression and cell survival by regulating phosphatidylinositol 3,4, 5–trisphosphate and Akt/protein kinase B signaling pathway"; Proc. Natl. Acad. Sci. USA 96: 6199–6204 (1999).
Giri, D., et al., "Inactivation of the PTEN tumor suppressor gene is associated with increased angiogenesis in clinically localized prostate carcinoma"; PubMed, Hum. Pathol. 30:419–24 [abstract] (1999).

* cited by examiner

*Primary Examiner*—Larry R. Helms
*Assistant Examiner*—Misook Yu
(74) *Attorney, Agent, or Firm*—Dann, Dortman, Herrell & Skillman

(57) ABSTRACT

Methods are provided for the identification, biochemical characterization and therapeutic use of agents which impact PTEN, p53, PI-kinase and AKT mediated cellular signaling.

3 Claims, 25 Drawing Sheets

Anti-VEGF Immunoblot

Figure 13

Allele: wt [ HA-wt [ GR [ wt [ HA-wt [ GR [
         +    +  -   +  -    -  +    +  -   +  -
MuristironeA: -   -   +    +   +    +   -

Blot: phospho S473 Akt      Akt

```
              1760      1770      1780      1790      1800
         ACAAAATGTTTCACTTTTGGGTAAATACGTTCTTCATACCAGGACCAGAG
         TGTTTTACAAAGTGAAAACCCATTTATGCAAGAAGTATGGTCCTGGTCTC
          D  K  M  F  H  F  W  V  N  T  F  F  I  P  G  P  E>
         ___HOMOLOG OF HUMAN MUTATED IN MULTIPLE ADVANC____>

>ClaI
                                                         |
                                                        >BsiXI
                                                         |
                                         >BsiQI         >TaqI
                                           |             |
              1810      1820      1830    |1840         1850
         GAAACCTCAGAAAAAGTGGAAAATGGAAGTCTTTGTGATCAGGAAATCGA
         CTTTGGAGTCTTTTTCACCTTTTACCTTCAGAAACACTAGTCCTTTAGCT
          E  T  S  E  K  V  E  N  G  S  L  C  D  Q  E  I  D>
         ___HOMOLOG OF HUMAN MUTATED IN MULTIPLE ADVANC____>

>RsaI
                                                         |
              1860      1870      1880      1890         1900
         TAGCATTTGCAGTATAGAGCGTGCAGATAATGACAAGGAGTATCTTGTAC
         ATCGTAAACGTCATATCTCGCACGTCTATTACTGTTCCTCATAGAACATG
            S  I  C  S  I  E  R  A  D  N  D  K  E  Y  L  V>
         ___HOMOLOG OF HUMAN MUTATED IN MULTIPLE ADVANC____>

1910      1920      1930      1940      1950
         TCACCCTAACAAAAAACGATCTTGACAAAGCAAACAAAGACAAGGCCAAC
         AGTGGGATTGTTTTTTGCTAGAACTGTTTCGTTTGTTTCTGTTCCGGTTG
          L  T  L  T  K  N  D  L  D  K  A  N  K  D  K  A  N>
         ___HOMOLOG OF HUMAN MUTATED IN MULTIPLE ADVANC____>

1960      1970      1980      1990      2000
         CGATACTTCTCTCCAAATTTTAAGGTGAAACTATACTTTACAAAAACAGT
         GCTATGAAGAGAGGTTTAAAATTCCACTTTGATATGAAATGTTTTTGTCA
          R  Y  F  S  P  N  F  K  V  K  L  Y  F  T  K  T  V>
         ___HOMOLOG OF HUMAN MUTATED IN MULTIPLE ADVANC____>

2010      2020      2030      2040      2050
         AGAGGAGCCATCAAATCCAGAGGCTAGCAGTTCAACTTCTGTGACTCCAG
         TCTCCTCGGTAGTTTAGGTCTCCGATCGTCAAGTTGAAGACACTGAGGTC
          E  E  P  S  N  P  E  A  S  S  S  T  S  V  T  P>
         ___HOMOLOG OF HUMAN MUTATED IN MULTIPLE ADVANC____>

>BsiQI
                            |
              2060      2070      2080      2090      2100
         ATGTTAGTGACAATGAACCTGATCATTATAGATATTCTGACACCACTGAC
         TACAATCACTGTTACTTGGACTAGTAATATCTATAAGACTGTGGTGACTG
          D  V  S  D  N  E  P  D  H  Y  R  Y  S  D  T  T  D>
         ___HOMOLOG OF HUMAN MUTATED IN MULTIPLE ADVANC____>

>BscCI
                                                   |
              2110      2120      2130         |2140     2150
         TCTGATCCAGAGAATGAACCTTTTGATGAAGATCAGCATTCACAAATTAC
```

Fig. 20B (continued)

```
CTTCTGCCATCTCTCTCCTCCTTTTTCTTCAGCCACAGGCTCCCAGACAT
GAAGACGGTAGAGAGAGGAGGAAAAAGAAGTCGGTGTCCGAGGGTCTGTA
                                                 M>
                                                 __>

>EcoRV
                                        |
       960        970       980       990  |   1000
GACAGCCATCATCAAAGAGATCGTTAGCAGAAACAAAAGGAGATATCAAG
CTGTCGGTAGTAGTTTCTCTAGCAATCGTCTTTGTTTTCCTCTATAGTTC
   T  A  I  I  K  E  I  V  S  R  N  K  R  R  Y  Q>
   ___HOMOLOG OF HUMAN MUTATED IN MULTIPLE ADVANC___>

>TaqI
       |
      1010       1020      1030      1040      1050
AGGATGGATTCGACTTAGACTTGACCTATATTTATCCAAATATTATTGCT
TCCTACCTAAGCTGAATCTGAACTGGATATAAATAGGTTTATAATAACGA
   E  D  G  F  D  L  D  L  T  Y  I  Y  P  N  I  I  A>
   ___HOMOLOG OF HUMAN MUTATED IN MULTIPLE ADVANC___>

>PstI
             |
      1060   | 1070      1080      1090      1100
ATGGGATTTCCTGCAGAAAGACTTGAAGGTGTATACAGGAACAATATTGA
TACCCTAAAGGACGTCTTTCTGAACTTCCACATATGTCCTTGTTATAACT
   M  G  F  P  A  E  R  L  E  G  V  Y  R  N  N  I  D>
   ___HOMOLOG OF HUMAN MUTATED IN MULTIPLE ADVANC___>

1110       1120      1130      1140      1150
TGATGTAGTAAGGTTTTTGGATTCAAAGCATAAAAACCATTACAAGATAT
ACTACATCATTCCAAAAACCTAAGTTTCGTATTTTTGGTAATGTTCTATA
      D  V  V  R  F  L  D  S  K  H  K  N  H  Y  K  I>
      ___HOMOLOG OF HUMAN MUTATED IN MULTIPLE ADVANC___>

>PstI
                                                 |
      1160       1170      1180      1190      1200
ACAATCTATGTGCTGAGAGACATTATGACACCGCCAAATTTAACTGCAGA
TGTTAGATACACGACTCTCTGTAATACTGTGGCGGTTTAAATTGACGTCT
   Y  N  L  C  A  E  R  H  Y  D  T  A  K  F  N  C  R>
   ___HOMOLOG OF HUMAN MUTATED IN MULTIPLE ADVANC___>

1210       1220      1230      1240      1250
GTTGCACAGTATCCTTTTGAAGACCATAACCCACCACAGCTAGAACTTAT
CAACGTGTCATAGGAAAACTTCTGGTATTGGGTGGTGTCGATCTTGAATA
    V  A  Q  Y  P  F  E  D  H  N  P  P  Q  L  E  L  I>
    ___HOMOLOG OF HUMAN MUTATED IN MULTIPLE ADVANC___>

>BglII
            |
      1260   |1270       1280      1290      1300
CAAACCCTTCTGTGAAGATCTTGACCAATGGCTAAGTGAAGATGACAATC
GTTTGGGAAGACACTTCTAGAACTGGTTACCGATTCACTTCTACTGTTAG
    K  P  F  C  E  D  L  D  Q  W  L  S  E  D  D  N>
    ___HOMOLOG OF HUMAN MUTATED IN MULTIPLE ADVANC___>
```

Fig. 20B

```
              1310      1320      1330      1340      1350
        ATGTTGCAGCAATTCACTGTAAAGCTGGAAAGGGACGGACTGGTGTAATG
        TACAACGTCGTTAAGTGACATTTCGACCTTTCCCTGCCTGACCACATTAC
         H  V  A  A  I  H  C  K  A  G  K  G  R  T  G  V  M>
         ___HOMOLOG OF HUMAN MUTATED IN MULTIPLE ADVANC____>

1360      1370      1380      1390      1400
        ATTTGTGCATATTTATTGCATCGGGGCAAATTTTTAAAGGCACAAGAGGC
        TAAACACGTATAAATAACGTAGCCCCGTTTAAAAATTTCCGTGTTCTCCG
          I  C  A  Y  L  L  H  R  G  K  F  L  K  A  Q  E  A>
         ___HOMOLOG OF HUMAN MUTATED IN MULTIPLE ADVANC____>

1410      1420      1430      1440      1450
        CCTAGATTTTTATGGGGAAGTAAGGACCAGAGACAAAAAGGGAGTCACAA
        GGATCTAAAAATACCCCTTCATTCCTGGTCTCTGTTTTTCCCTCAGTGTT
          L  D  F  Y  G  E  V  R  T  R  D  K  K  G  V  T>
         ___HOMOLOG OF HUMAN MUTATED IN MULTIPLE ADVANC____>

1460      1470      1480      1490      1500
        TTCCCAGTCAGAGGCGCTATGTATATTATTATAGCTACCTGCTAAAAAAT
        AAGGGTCAGTCTCCGCGATACATATAATAATATCGATGGACGATTTTTTA
          I  P  S  Q  R  R  Y  V  Y  Y  Y  S  Y  L  L  K  N>
         ___HOMOLOG OF HUMAN MUTATED IN MULTIPLE ADVANC____>

1510      1520      1530      1540      1550
        CACCTGGATTACAGACCCGTGGCACTGCTGTTTCACAAGATGATGTTTGA
        GTGGACCTAATGTCTGGGCACCGTGACGACAAAGTGTTCTACTACAAACT
          H  L  D  Y  R  P  V  A  L  L  F  H  K  M  M  F  E>
         ___HOMOLOG OF HUMAN MUTATED IN MULTIPLE ADVANC____>

1560      1570      1580      1590      1600
        AACTATTCCAATGTTCAGTGGCGGAACTTGCAATCCTCAGTTTGTGGTCT
        TTGATAAGGTTACAAGTCACCGCCTTGAACGTTAGGAGTCAAACACCAGA
            T  I  P  M  F  S  G  G  T  C  N  P  Q  F  V  V>
         ___HOMOLOG OF HUMAN MUTATED IN MULTIPLE ADVANC____>

1610      1620      1630      1640      1650
        GCCAGCTAAAGGTGAAGATATATTCCTCCAATTCAGGACCCACGCGGCGG
        CGGTCGATTTCCACTTCTATATAAGGAGGTTAAGTCCTGGGTGCGCCGCC
          C  Q  L  K  V  K  I  Y  S  S  N  S  G  P  T  R  R>
         ___HOMOLOG OF HUMAN MUTATED IN MULTIPLE ADVANC____>

>RsaI
                   |
              1660 |    1670      1680      1690      1700
        GAGGACAAGTTCATGTACTTTGAGTTCCCTCAGCCATTGCCTGTGTGTGG
        CTCCTGTTCAAGTACATGAAACTCAAGGGAGTCGGTAACGGACACACACC
          E  D  K  F  M  Y  F  E  F  P  Q  P  L  P  V  C  G>
         ___HOMOLOG OF HUMAN MUTATED IN MULTIPLE ADVANC____>

>EcoRV
          |
          |  1710      1720      1730      1740      1750
        TGATATCAAAGTAGAGTTCTTCCACAAACAGAACAAGATGCTCAAAAAGG
        ACTATAGTTTCATCTCAAGAAGGTGTTTGTCTTGTTCTACGAGTTTTTCC
          D  I  K  V  E  F  F  H  K  Q  N  K  M  L  K  K>
         ___HOMOLOG OF HUMAN MUTATED IN MULTIPLE ADVANC____>
```

Fig. 20B (continued)

```
AGACTAGGTCTCTTACTTGGAAAACTACTTCTAGTCGTAAGTGTTTAATG
 S   D   P   E   N   E   P   F   D   E   D   Q   H   S   Q   I   T>
___HOMOLOG OF HUMAN MUTATED IN MULTIPLE ADVANC____>

2160
AAAAGTCTGA
TTTTCAGACT
 K   V   *>
```

Fig. 20B (continued)

COMPOSITIONS AND METHODS FOR IDENTIFYING AGENTS WHICH MODULATE PTEN FUNCTION AND PI-3 KINASE PATHWAYS

This invention claims priority under 35 U.S.C. §119(e) to U.S. Provisional Application Nos. 60/208,437 and 60/274,167 filed May 30, 2000 and Mar. 8, 2001 respectively. The entire disclosures of each of the above-identified applications is incorporated by reference herein.

Pursuant to 35 U.S.C. §202(c), it is hereby acknowledged that the U.S. Government has certain rights in the invention described herein, which was made in part with funds from the National Institutes of Health, Grant Nos: RO1CA75637.

FIELD OF THE INVENTION

This invention relates to the treatment of neoplastic disease and other pathological conditions characterized by cellular hyperproliferation and loss of regulated growth and motility. More specifically, this invention provides methods for the identification and characterization of agents which modulate PTEN, PI-3 kinase and AKT activity.

BACKGROUND OF THE INVENTION

Various scientific and scholarly articles are cited throughout the specification. These articles are incorporated by reference herein to describe the state of the art to which this invention pertains.

The reversible phosphorylation of proteins and lipids is critical to the control of signal transduction in mammalian cells and is regulated by kinases and phosphatases (Hunter 1995). The product of the tumor suppressor gene PTEN/MMAC (hereafter termed PTEN) was identified as a dual specificity phosphatase and has been shown to dephosphorylate inositol phospholipids in vivo (Li et al Science 1997, Steck et al 1997, Li et al Cancer Res 1997,Myers et al, 1997, Myers et al 1998, Maehama et al, 1998, Stambolic et al 1998, Wu et al 1998). The PTEN gene, which is located on the short arm of chromosome 10 (10q23), is mutated in 40–50% of high grade gliomas as well as many other tumor types, including those of the prostate, endometrium, breast, and lung (Li et al, Science 1997, Steck et al 1997, Maier et al 1998). In addition, PTEN is mutated in several rare autosomal dominant cancer predisposition syndromes, including Cowden disease, Lhermitte-Duclos disease and Bannayan-Zonana syndrome (Liaw et al 1997, Myers et al AJHG 1997, Maehama et al TCB 1999, Cantley and Neel 1999). Furthermore, the phenotype of PTEN-knockout mice revealed a requirement for this phosphatase in normal development and confirmed its role as a tumor suppressor (Podsypanina et al PNAS 1999, Suzuki et al Curr Biol 1998, Di Christofano et al Nat Gen 1998).

PTEN is a 55 kDa protein comprising an N-terminal catalytic domain, identified as a segment with homology to the cytoskeletal protein tensin and containing the sequence $HC(X)_5R$ (SEQ ID NO: 22), which is the signature motif of members of the protein tyrosine phosphatase family, and a C-terminal C2 domain with lipid-binding and membrane-targeting functions (Lee et al Cell 1999). The sequence at the extreme C-terminus of PTEN is similar to sequences known to have binding affinity for PDZ domain-containing proteins. PTEN is a dual specificity phosphatase that displays a pronounced preference for acidic substrates (Myers et al PNAS 1997). Importantly, PTEN possesses lipid phosphatase activity, preferentially dephosphorylating phosphoinositides at the D3 position of the inositol ring. It is one of two enzymes known to dephosphorylate the D3 position in inositol phospholipids.

Since solid tumor progression is dependent on the induction of angiogenic signals and augmented angiogenesis contributes to the high mortality associated with many cancers, there is a need to elucidate the cellular components that participate in these processes. The urgency of such investigations is underscored by the fatal nature of highly malignant brain tumors and the fact that the degree of tumor invasiveness is directly correlated with enhanced angiogenesis. Furthermore, elucidation of cellular components that contribute to the angiogenic switch facilitates the identification of therapeutic agents and delivery methods useful for the treatment of such malignant diseases.

PTEN phosphatase activity has also been implicated in many cellular biochemical reactions. It is an object of the invention to also provide methods for the identification of agents which impact PTEN modulation of immunoreceptors, AKT, PI3 kinase and p53 signaling. Methods of use of agents so identified are also within the scope of the invention.

SUMMARY OF THE INVENTION

PTEN is a pivotal signaling molecule which modulates a wide variety of cellular processes. These cellular processes include angiogenesis, cellular migration, immunoreceptor modulation, p53 signaling and apoptotic cell death, PI3 and AKT signaling. Mutations in PTEN have been associated with the highly malignant progression of brain tumors. A hallmark of this malignant progression is a dramatic increase in angiogenesis and invasiveness mediated by the concomitant formation of new blood vessels.

Thus, in accordance with the present invention methods for the treatment of cancer associated with PTEN mutation are provided. Exemplary methods include delivery of a native PTEN encoding nucleic acid to cancer cells such that the native PTEN protein is expressed. Additional methods for the treatment of cancer in accordance with the present invention entail the administration of at least one agent selected from the group consisting of PTEN agonists, PI3 kinase inhibitors and AKT inhibitors. The aforementioned treatment protocols may also comprise the administration of conventional chemotherapeutic agents.

In another aspect of the invention, methods for the prevention of aberrant angiogenesis are also provided. Aberrant angiogenesis is associated with several diseases. These include not only cancer, but autoimmune disease, arthritis, systemic lupus erthymatosis, inflammatory bowel disease, coronary artery disease, cerebrovascular disease, and atherosclerosis. Methods for the administration of at least one agent selected from the group consisting of native PTEN encoding nucleic acids, PTEN agonists, PI3 kinase inhibitors and AKT inhibitors for the inhibition or prevention of aberrant angiogenesis are also disclosed herein.

PTEN has also been implicated in immunoreceptor modulation. Thus, in yet another aspect of the invention, methods for inhibiting the immune response in target cells are provided. PTEN agonists, PI3 kinase inhibitors and/or AKT inhibitors are administered to patients to prevent or inhibit immunoreceptor signaling. Such agents should have efficacy in the treatment of graft rejection or graft versus host disease.

In yet another aspect of the invention, methods for regulating p53 mediated gene expression are also provided. Such methods entail the administration of native PTEN, PTEN agonists and/or PI3 kinase inhibitors or AKT inhibitors to induce functional p53 in tumor cells. Such agents effectively increase chemosensitivity and/or radiosensitivity of tumor cells by stimulating p53 mediated apoptotic cell death.

Given the widespread effects of PTEN, methods for identifying agents which modulate PTEN activity are also provided. Exemplary assays include those which assess alterations in activated AKT levels, alterations in microvessel formation, alterations in TSP1 levels, alterations in VEGF levels, alterations in TIMP3 levels, alterations in MMP9 activation and alterations PTEN phosphatase activity levels in the presence and absence of such test agents.

Also provided in accordance with the present invention are high throughput screening methods for identifying small molecules which have affinity for PTEN or fragments thereof. Small molecules so identified are within the scope of the present invention and may optionally be further characterized in the functional assays described above.

BRIEF DESCRIPTION OF THE DRAWINGS

(FIG. 1A) Cell lysates from the U87MG (U87) cell line and U87 cells infected with a retroviral vector encoding PTEN (pBabe-Puro-PTEN) or mutants of PTEN (pBabe-Puro-PTEN-G129E or R130M) were resolved by SDS-PAGE, equal amounts of proteins were loaded per lane and immunoblotted with antisera to PTEN, phospho-AKT and total AKT, and visualized by enhanced chemiluminescence. The basal levels of PTEN (top), phosphorylated AKT (ser 473) (middle) and total AKT (bottom) are shown. The status of the PTEN gene in each stable cell line was designated as: WT.E1 and WT.C7 two separate clones expressing wild type PTEN. R130M and G129E are mutated PTEN proteins. R130M is inert as both a protein and a lipid phosphatase. The G129E PTEN can dephosphorylate acidic phosphopeptides, but cannot dephosphorylate the lipid substrate, PIP3. The U87MG (U87) cell line is the parental cell line isolated from a human glioblastoma multiforme patient. (FIG. 1B) Comparison of in vitro growth of U87MG cells transduced with mutants of PTEN. Equal number of cells (1×105) were incubated in RPMI +10% FBS for different times and cell numbers were quantitated by direct cell counting.

(FIG. 2A) Cell growth in vivo. In order to determine the rate of cell growth in vivo, equal amount of cells ($5 \times 10^6$) from each cell line were implanted at the right ventral flank by subcutaneous injection (see legend). The formation and growth of the subcutaneous tumor was monitored and the volume of the tumor was determined by a three dimensional measurement at the times indicated (day 0, the date of implantation, no tumor is detected). Data were analyzed by Student's t-test and differences were significant comparing the PTEN deficient (U87MG, R130M, G129E) to the wild type PTEN (WT.E1, WT.C7), n=5, number of mice p<0.0001 (FIG. 2B) Stereophotography of subcutaneous tumor sites in mice implanted with the parental U87 tumor, PTEN minus (left panel) versus wild type PTEN reconstituted tumor cells (right panel). These tumors represent 25 and 42 days after implantation for PTEN minus versus wild type PTEN reconstituted tumors, respectively. (FIG. 2C) Immunoblot of cryostat tissue sections from subcutaneous tumor for the expression pattern of PTEN, AKT and phosphorylated AKT. Frozen tissue sections were solubilized in Laemmli sample buffer, total protein was quantitated and equal protein was loaded on SDS PAGE. The data shown are representative of tissue analysis from 5 animals per experimental group.

(FIG. 3C) Microvessel density (MVD) counts were performed on tumor tissue stained with anti-CD31 antibody to determine effect of expression of PTEN and specific PTEN mutants (G129E or R130M) on tumor induced angiogenesis. Bars represent standard deviation, 5 animals per group. Statistical analysis by Student's t-test demonstrate significant difference between MVD of PTEN null and PTEN catalytic mutants as compared to wild type PTEN reconstituted tumors, n=5, number of mice p<0.001. (FIG. 3D) PTEN regulates the expression of thrombospondin-1 (TSP-1) in U87MG cells. RNAase protection assay was used to measure levels of TSP-1 mRNA in wild type PTEN expressing U87 cells or cells transduced with a mutant catalytically dead PTEN (G129R). U87MG cells were infected with retrovirus encoding wild type PTEN (WT), the catalytically dead, G129R mutant (GR) or empty vector retrovirus (−) and selected for 10 days in puromycin. RNA was harvested and RNAase protection assays were carried out using probes for TSP-1 and GAPDH. A probe for glyceraldehyde phosphate dehydrogenase (GAPDH) was used as a normalization control. (FIG. 3E) Thrombospondin immunoblot analysis. U87MG transduced with wild type PTEN (WT) or a catalytic mutant PTEN (G129R) in an ecdysone inducible expression system were induced (48 hours) with 0.5 $\mu$M muristirone or assayed without induction to determine the effect of PTEN expression on the induction of TSP-1 by Western blotting. Supernatants from cells were prepared and proteins resolved on SDS-PAGE and probed with anti-TSP-1 antibody. There is clear up-regulation of TSP-1 in wild type PTEN transduced U87 cultures compared to U87 cells expressing the lipid phosphatase deficient G129R mutant PTEN.

(FIG. 5D) A G129E PTEN reconstituted tumor implanted into a nude mouse brain. (FIG. 5E) Survival plots for mice implanted with PTEN minus or parental U87 cells transduced with mutants of PTEN as shown. Survival data represents 15 animals per experimental group. n=15, p<0.0001 for difference observed between the PTEN + and PTEN − groups for survival.

(FIG. 9A) Quantitation of phagocytosis of IgG coated sRBCs by J774A.1 cells overexpressing D/N Syk. The columns indicate phagocytic index of uninfected J774A.1 cells, cells infected with vaccinia virus containing vector only and cells infected with vaccinia virus containing D/N Syk. (FIG. 9B) J774A.1 cells infected with vaccinia virus containing D/N Syk expressed D/N Syk protein as shown in lane 3, while lane 1 represents untreated J774A.1 cells and lane 2 represents J774A.1 cells infected with empty vector vaccinia virus as a control. The error bars represent standard deviation of the mean.

(FIG. 10A) PP1 blocks the phagocytosis significantly at 10 $\mu$M concentration and the effect is dose-dependent. (FIG. 10B) Wortmannin blocks phagocytosis significantly at 5 $\mu$g/ml. The columns indicate phagocytic index of untreated J774A.1 cells treated with DMSO (control), PP1, or wortmannin. The error bars represent standard deviation of mean.

FIG. 11A, upper panel shows the effects of D/N Syk on tyrosine phosphorylation of Cbl in response to stimulation with sensitized sRBCs. Lysates prepared from resting cells or cells stimulated with sRBCs for 5 minutes were immunoprecipitated with polyclonal anti-Cbl Ab and immunoblotted with anti-phosphotyrosine antibody. Lane 2 represents Cbl immunoprecipitated from resting J774A.1 cells while lanes 5 and 8 represent Cbl immunoprecipitated from resting J774A.1 cells infected with vaccinia virus containing plain vector or dominant negative Syk respectively. Lane 3 represents Cbl IP from cells stimulated with sRBCs while lane 6 and 9 represents Cbl IP from cells infected with vaccinia virus containing plain vector or dominant negative Syk respectively stimulated with sRBCs. (FIG. 11B, Upper panel) Cells were treated with PP1 to evaluate the role of the Src family kinases in Cbl tyrosine phosphorylation following stimulation with sensitized sRBCs. Lysates prepared from resting cells or cells stimulated with sRBCs for 5 minutes were immunoprecipitated with polyclonal anti-Cbl Ab and the resultant Cbl immunoprecipitates (Cbl IP) were immunoblotted with anti-phosphotyrosine antibody. Lane 2 represents Cbl IP from resting J774A.1 cells while lane 5 represents Cbl IP from resting J774A.1 cells treated with 10 $\mu$M PP1. Lane 3 represents Cbl IP from cells stimulated with sRBCs while lane 6 represents Cbl IP from cells treated with PP1 and stimulated with sRBCs. (FIGS. 11A and 11B, lower panels) Anti-Cbl immunoblot of Cbl IP. Lysates prepared from resting cells or cells stimulated with sRBCs for 5 minutes were immunoprecipitated with anti-Cbl antisera and immunoblotted with anti-Cbl antisera. Lanes are as designated in (A).

FIG. 13 is a Western blot showing that PTEN regulates phospho-AKT levels. A muristirone inducible expression system was used to express PTEN or PTEN mutants in U87MG cells. Immunoblots of lysates derived from U87 cells +/− induction for expression of wild type PTEN, wild type HA-tagged PTEN, or G129R (GR) PTEN mutant of PTEN. were probed with antibodies specific for phospho-(S473)AKT or AKT.

FIG. 20B depicts a PTEN encoding nucleic acid (SEQ ID NO: 1; shown in double-stranded form) and the amino acid sequence (SEQ ID NO: 2) of PTEN.

DETAILED DESCRIPTION OF THE INVENTION

Figure 1A:
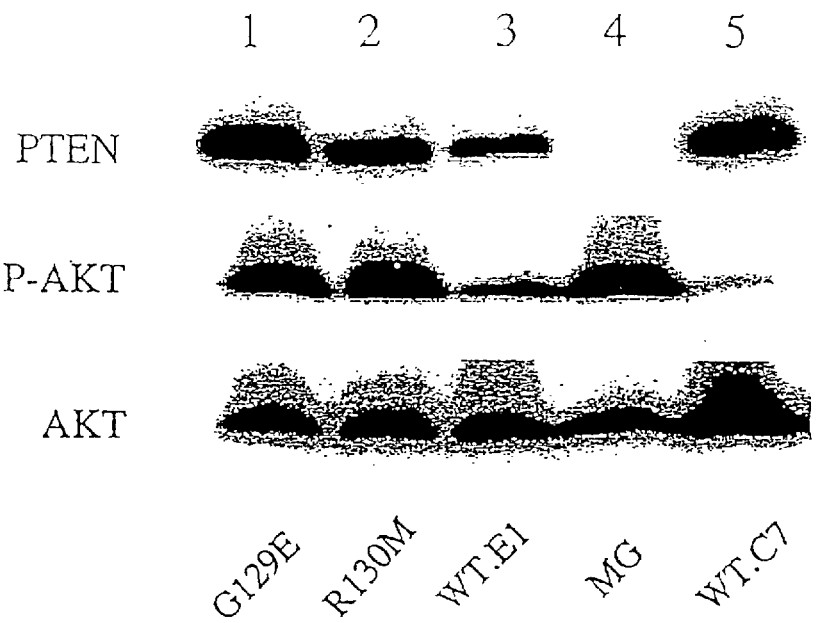
FIGS. 1A and 1B are a Western blot and a graph showing that stable expression of PTEN and PTEN mutants in U87MG cells regulates AKT.

Tumor progression, particularly in aggressive and malignant tumors, is associated with the induction of angiogenesis, a process termed the angiogenic switch. Mutations of the tumor suppressor PTEN, a phosphatase with specificity for D3 phosphorylated inositol phospholipids, are associated with malignant and invasive tumor progression. PTEN is, therefore, a critical regulator of tumor progression that acts by modulating the angiogenic switch response.

To address the role of PTEN in the angiogenic switch response, a critical predictor of the metastatic potential of a tumor, a model system was developed utilizing the U87MG glioma cell line. The U87MG cell line, which is null for PTEN, is a highly metastatic cell line derived from a human glioblastoma multiforme patient. U87MG glioma cells stably reconstituted with PTEN cDNA were tested for growth in a nude mouse orthotopic brain tumor model. The introduction of wild type PTEN into U87MG cells results in decreased tumor growth in vivo and prolonged survival of mice implanted intracranially with these cells. PTEN reconstitution diminished phosphorylation of AKT within the PTEN-reconstituted tumor, induced thrombospondin 1 expression, and suppressed VEGF expression and angiogenic activity. These effects were not observed in tumors reconstituted with the G129E mutant form of PTEN, in which lipid phosphatase activity is ablated. These data provide the first direct evidence that PTEN coordinately regulates the angiogenic switch and the progression of gliomas to a malignant phenotype via the regulation of phosphoinositide-dependent signals which control p53 transcriptional activity.

Thus in accordance with the present invention, methods are provided for identifying and characterizing small molecules which impact PTEN modulated angiogenesis and tumor progression. A variety of biochemical assays are provided which will facilitate the characterization of such molecules. Exemplary assays include those suitable for assessing matrix degradation, angiogenesis, tumor invasion and suppression of matrix metalloproteinase 9 activity.

The regulatory role for PTEN phosphatase is widespread throughout the cell. As described in Example III, PTEN also regulates inflammatory signaling. Immunoreceptor activation is associated with antibody dependent cell mediated toxicity, NK and CTL lysis of target cells, such as tumor cells, parasitic cells and microorganisms. The data presented herein indicate that PTEN controls immunoreceptor desensitization in vivo. This observation provides the basis for the development of assays and methods to identify and characterize small molecules which have efficacy in the treatment immune disorders associated with hyperactive inflammatory responses. Such molecules should also have efficacy in the treatment of graft versus host disease and graft rejection. Methods of use of agents so identified are also in the scope of the invention. PTEN inhibitors should effectively block immunoreceptor desensitization thereby augmenting the immunotherapeutic activity of immune cells. Immune cells that may be targeted with these inhibitors include T cells, B cells, macrophages, dendritic cells, neutrophils, mast cells, eosinophils, and platelets.

A detailed analysis of the PTEN and PI-3 kinase signaling cascade and its impact on p53 mediated transcription is provided in Example IV. In accordance with the present invention, it has been discovered that p53 mediated transcription is dependent upon proper PTEN/PI3 kinase signaling. These data also indicate that PI-3 kinase inhibitors have in vivo antiangiogenic activity. It has also been discovered that PTEN exerts control over p53 levels in cells as cells that contain mutated PTEN have a marked reduction in functional p53 levels. Reduced p53 function is associated with reduced sensitivity to stress or chemotherapy induced apoptosis. Thus, this data provides the basis for the development of additional biological assays for assessing the effects of small molecules which inhibit PTEN/PI3 kinase/p53 signaling. Such small molecules should also have efficacy in the treatment of cancer.

PTEN activity has also been implicated in chemo- and radio-sensitivity as set forth in Example V. Thus, based on the data presented herein, it has been discovered that activation of PTEN and the PI3 kinase pathway sensitizes cells to p53 mediated cell death through the control of p53 induced apoptosis. These observations thus provide the basis for additional methods for identifying efficacious chemotherapeutic combination therapies which should be effective in the treatment of cancer.

The following description sets forth the general procedures involved in practicing the present invention. To the extent that specific materials are mentioned, it is merely for purposes of illustration and is not intended to limit the invention. Unless otherwise specified, general cloning and gene expression procedures, such as those set forth in Current Protocols in Molecular Biology, Ausubel et al. eds., JW Wiley and Sons, NY (1998)are utilized.

I. Definitions

Various terms relating to the biological molecules of the present invention are used hereinabove and also throughout the specifications and claims.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The present invention also includes methods of use for active portions, fragments, derivatives and functional or non-functional mimetics of PTEN polypeptides or proteins of the invention. An "active portion" of PTEN polypeptide means a peptide that is less than the full length PTEN polypeptide, but which retains measurable biological activity.

A "fragment" or "portion" of the PTEN polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the PTEN polypeptide sequence, antigenic determinants, or epitopes are useful for eliciting immune responses to a portion of the PTEN amino acid sequence.

A "derivative" of the PTEN polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of the original PTEN polypeptide.

As mentioned above, the PTEN polypeptide or protein of the invention includes any analogue, fragment, derivative or mutant which is derived from a PTEN polypeptide and which retains at least one property or other characteristic of the PTEN polypeptide. Different "variants" of the PTEN polypeptide exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the PTEN polypeptide, (c) variants in which one or more amino acids include a substituent group, and (d) variants in which the PTEN polypeptide is fused with another peptide or polypeptide such as a fusion partner, a protein tag or other chemical moiety, that may confer useful properties to the PTEN polypeptide, such as, for example, an epitope for an antibody, a polyhistidine sequence, a biotin moiety and the like. Other PTEN polypeptides of the invention include variants in which amino acid residues from one species are substituted for the corresponding residues in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of the PTEN polypeptide that retain any of the biological properties of the PTEN polypeptide, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specfically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

Amino acid residues described herein are preferred to be in the "L" isomeric form. However, residues in the "D" isomeric form may be substituted for any L-amino acid residue, provided the desired properties of the polypeptide are retained.

All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50–60% by weight of a given material (e.g., nucleic acid, oligonucleotide, protein, etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitate isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other manners, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

Figure 20A:
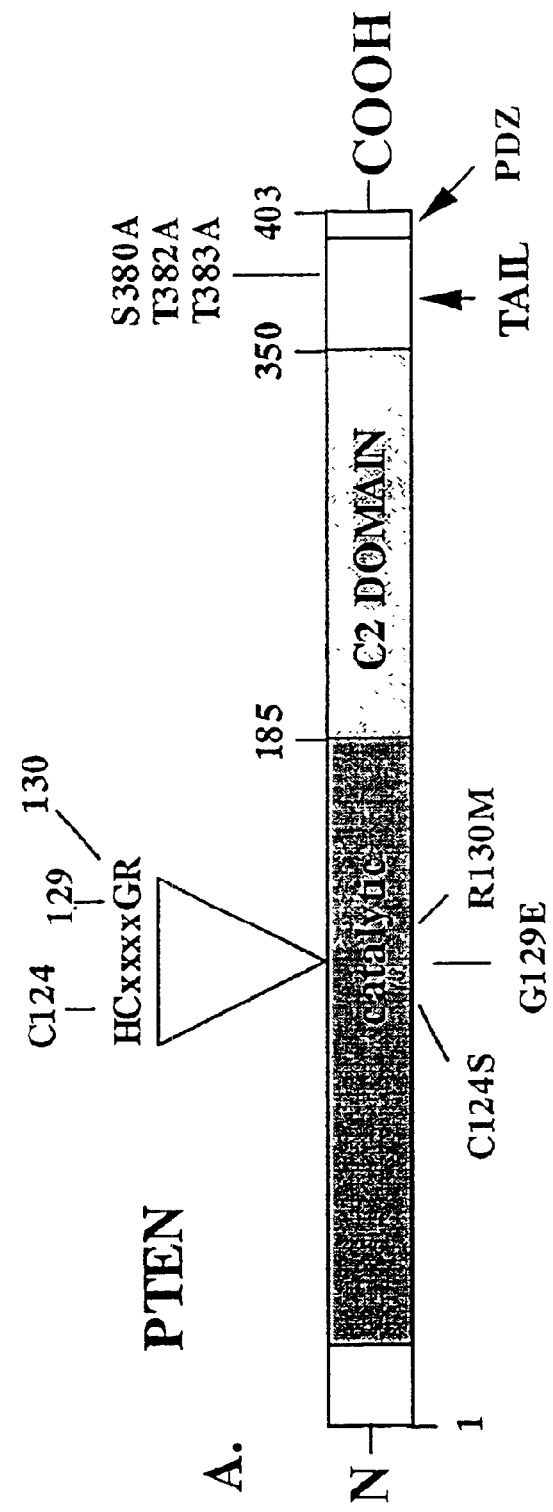
FIG. 20A is a schematic representation of PTEN. A PTEN sequence (SEQ ID NO: 23) which matches the signature sequence motif of protein tyrosine phosphatases is also shown.

II. Preparation of PTEN-Encoding Nucleic Acid Molecules, PTEN Proteins and Antibodies Thereto The PTEN protein comprises, from amino- to carboxy-terminus, a protein tyrosine phosphatase catalytic domain that has considerable homology to the cytoskeletal protein tensin, a C2 domain that confers lipid-binding and membrane-targeting, and a PDZ domain-binding site that contributes to membrane localization and protein stability (Lee et al Cell 1999, Wu et al PNAS 2000;). The amino-terminal catalytic domain includes the $HC(X)_5R$ sequence (SEQ ID NO: 22), which is the signature motif of protein tyrosine phosphatases. The Genbank accession number for the human PTEN encoding nucleic acid molecule is NM000313. The amino acid sequence of PTEN is provided in FIG. 20B. These sequences are also referred to herein as SEQ ID NO: 1 and SEQ ID NO: 2.

The PTEN protein, hereafter termed PTEN, is classified as a dual specificity phosphatase, whose substrate targets include phosphorylated proteins and inositol phospholipids. PTEN is distinguished by the fact that, unlike other dual specificity phosphatases, it preferentially dephosphorylates phosphoinositides at the D3 position of the inositol ring (Maehama et al Trends Cell Biol. 1999, Maehama et al J Biol Chem 1998). PTEN is the product of the tumor suppressor gene PTEN/MMAC, mutations in which have been correlated with a number of different tumor types, including those of the brain, prostate, endometrium, breast, and lung.

A. Nucleic Acid Molecules

Nucleic acid molecules encoding PTEN may be prepared by two general methods: (1) They may be synthesized from appropriate nucleotide triphosphates, or (2) they may be isolated from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a large double-stranded DNA molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct the entire protein encoding sequence. A synthetic DNA molecule so constructed may then be cloned and amplified in an appropriate vector.

Nucleic acid sequences encoding PTEN may be isolated from appropriate biological sources using methods known in the art. In a preferred embodiment, a cDNA clone is isolated from an expression library of human origin. In an alternative embodiment, genomic clones encoding PTEN may be isolated.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable E. coli host cell.

PTEN-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as agents to inhibit or augment PTEN activity in cells or tissues. In particular, the present invention describes the use of PTEN encoding nucleic acids for reconstitution of PTEN activity in malignant cells or tissues for the purposes anti-cancer therapy.

B. Proteins

Full-length PTEN of the present invention may be prepared in a variety of ways, according to known methods. The protein may be purified from appropriate sources, e.g., human or animal cultured cells or tissues, by immunoaffinity purification. However, this is not a preferred method due to the small amounts of protein likely to be present in a given cell type at any time. The availability of nucleic acids molecules encoding PTEN enables production of the protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of PTEN may be produced by expression in a suitable procaryotic or eucaryotic system. For example, part or all of a DNA molecule, such as the cDNA having Sequence I.D. No. 1, may be inserted into a plasmid vector adapted for expression in a bacterial cell, such as *E. coli*, or into a baculovirus vector for expression in an insect cell. Such vectors comprise the regulatory elements necessary for expression of the DNA in the bacterial host cell, positioned in such a manner as to permit expression of the DNA in the host cell. Such regulatory elements required for expression include promoter sequences, transcription initiation sequences and, optionally, enhancer sequences.

The PTEN produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The PTEN proteins of the invention, prepared by the aforementioned methods, may be analyzed according to standard procedures. For example, such proteins may be subjected to amino acid sequence analysis, according to known methods.

The present invention also provides methods of use of antibodies capable of immunospecifically binding to proteins of the invention. Polyclonal antibodies directed toward PTEN or fragments thereof may be prepared according to standard methods. In a preferred embodiment, monoclonal antibodies are prepared, which react immunospecifically with various epitopes of PTEN. Monoclonal antibodies may be prepared according to general methods of Köhler and Milstein, following standard protocols. Polyclonal or monoclonal antibodies that immunospecifically interact with PTEN can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-PTEN antibodies are described below.

III. Uses of PTEN-Encoding Nucleic Acids, PTEN Proteins and Antibodies Thereto

Tumor suppressor proteins constitute a functional family of proteins known to be essential regulators of cellular proliferation and, as such, provide suitable targets for the development of therapeutic agents for modulating their activity in a cell. Since PTEN is a tumor suppressor protein implicated in the etiology of many malignant diseases, methods for identifying agents that modulate its activity are provided. Agents so identified should have efficacy in the treatment of a variety of malignant diseases. The use of PTEN modulating agents in conjunction with other known anti-cancer treatments such as chemotherapy and radiation therapy is also described. Moreover, such therapeutic agents will also be useful for modulating the activity of PTEN in other cellular systems. Since there are several diseases, other than cancer, in which abnormal angiogenesis contributes to the etiology of the disease, the administration of PTEN modulating agents should provide therapeutic advantages for the treatment of these conditions. Utilization of therapeutic agents that modulate PTEN activity could also be used effectively to treat disorders characterized hyperactivity of the inflammatory immune response.

A. PTEN-Encoding Nucleic Acids

PTEN-encoding nucleic acids may be used for a variety of purposes in accordance with the present invention. PTEN-encoding DNA, RNA, or fragments thereof may be used as probes to detect the presence of and/or expression of genes encoding PTEN. Methods in which PTEN-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

Nucleic acid molecules, or fragments thereof, encoding PTEN may also be utilized to control the expression of PTEN, thereby regulating the amount of protein available to participate in tumor suppressor signaling pathways. Alterations in the physiological amount of PTEN may act synergistically with chemotherapeutic agents used to treat cancer. In one embodiment, the nucleic acid molecules of the invention will be used to restore PTEN expression to normal cellular levels or overexpress PTEN in a population of malignant cells. In this embodiment, reconstitution of signaling events downstream of PTEN abrogates the aberrant cellular proliferation observed in malignant cells.

In another embodiment, the nucleic acid molecules of the invention may be used to decrease expression of PTEN in a population of target cells. In this embodiment, oligonucleotides are targeted to specific regions of PTEN-encoding genes that are critical for gene expression. The use of antisense oligonucleotides to decrease expression levels of a pre-determined gene is known in the art. In a preferred embodiment, such antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art. The use of antisense oligonucleotides for the modulation of PTEN expression is disclosed in U.S. Pat. No. 6,020,199, filed Feb. 1, 2000, the entire disclosure of which is incorporated by reference.

As described above, PTEN-encoding nucleic acids are also used to advantage to produce large quantities of substantially pure PTEN protein, or selected portions thereof. In a preferred embodiment, the N-terminal "catalytic domain" of PTEN is produced by expression of a nucleic acid encoding the domain. The full-length protein or selected domain is thereafter used for various research, diagnostic and therapeutic purposes, as described below.

B. PTEN Protein and Antibodies

Purified PTEN, or fragments thereof, may be used to produce polyclonal or monoclonal antibodies which also may serve as sensitive detection reagents for the presence and accumulation of PTEN (or complexes containing PTEN) in cultured cells or tissues from living patients (the term "patients" refers to both humans and animals). Recombinant techniques enable expression of fusion proteins containing part or all of the PTEN protein. The full length protein or fragments of the protein may be used to advantage to generate an array of monoclonal antibodies specific for various epitopes of the protein, thereby providing even greater sensitivity for detection of the protein in cells or tissue.

Polyclonal or monoclonal antibodies immunologically specific for PTEN may be used in a variety of assays designed to detect and quantitate the protein, which may be useful for diagnosing a PTEN-related malignant disease in a patient. Such assays include, but are not limited to: (1) flow cytometric analysis; (2) immunochemical localization of PTEN in cultured cells or tissues; and (3) immunoblot analysis (e.g., dot blot, Western blot) of extracts from various cells and tissues. Additionally, as described above, anti-PTEN can be used for purification of PTEN (e.g., affinity column purification, immunoprecipitation).

Anti-PTEN antibodies may also be utilized as therapeutic agents to block the normal functionality of PTEN in a target cell population, such as an inflammatory cell. Thus, similar to the antisense oligonucleotides described above, anti-PTEN antibodies may be delivered to a target cell population by methods known in the art (i.e. through various lipophilic carriers that enable delivery of the compound of interest to the target cell cytoplasm) where the antibodies may interact with intrinsic PTEN to render itx nonfunctional.

From the foregoing discussion, it can be seen that PTEN-encoding nucleic acids and PTEN proteins of the invention can be used to modulate PTEN gene expression and protein activity for the purposes of assessing the impact of PTEN modulation on the regulation of proliferative pathways of a cell or tissue sample. It is expected that these tools will be particularly useful for the treatment of human neoplastic disease in that PTEN-encoding nucleic acids, proteins and antibodies are excellent candidates for use as therapeutic agents.

Although the compositions of the invention have been described with respect to human therapeutics, it will be apparent to one skilled in the art that these tools will also be useful in animal and cultured cell experimentation with respect to various malignancies and/or other conditions manifested by alterations in cellular proliferation. As therapeutics, they can be used either alone or as adjuncts to other chemotherapeutic drugs to improve the effectiveness of such anti-cancer agents.

III. Therapeutics

A. Rational Drug Design

Since PTEN is a tumor suppressor protein implicated in the etiology of many malignant diseases, including, but not limited to, those of the brain, prostate, endometrium, and lung, methods for identifying agents that modulate its activity should result in the generation of efficacious therapeutic agents for the treatment of a variety of malignant and inflammatory diseases.

The crystal structure of PTEN, solved in 1999, revealed that the 403 amino acid protein comprises three domains of known function. These are the N terminal catalytic domain (residues 1–185), the C2 domain (residues 186–349) that participates in membrane binding and catalysis and the C terminal tail region (residues 350–403). See FIG. 20. Each of these domains provide suitable targets for the rational design of therapeutic agents which modulate PTEN activity. Particularly preferred regions are the N terminal and C2 domains, specifically regions including certain unique residues within and adjacent to the P loop, the WPD loop and the TI loop. It is these residues that participate in specific PIP3 substrate recognition and catalysis thereof. Another suitable region includes the C terminal tail which participates in PTEN regulatory and degradation in vivo. Small peptide molecules corresponding to these regions may be used to advantage in the design of therapeutic agents which effectively modulate the activity of PTEN, PI-3 kinase cascades, AKT cascades, as well as p53-mediated transcription and cell death.

PTEN is phosphorylated on tyrosine, serine and threonine residues. Agents which affect the phosphorylation state of the protein will also be screened as those small molecules which affect phosphorylation of PTEN should also modulate PTEN interactions with other proteins. The DLDLTYIYP motif (residues 22–30; SEQ ID NO: 3) at the extreme N terminus of PTEN contains a YxxP motif (SEQ ID NO: 4), a possible docking site for adapter proteins like crk and crkl via SH2 interactions. Another motif, YFSPN (SEQ ID NO: 5) in the C terminus has been identified as the binding site for crk and crkl. The YLVLTL motif (SEEQ ID NO: 6) in the extreme C terminus is a site for SH2 interactions with Shc or SHP-1. The YSYL motif (SEQ ID NO: 7), which contains a tyrosine at position 178, is 100% conserved from Drosophila to man. Other tyrosine phosphorylated motifs include: YRNNIDD (SEQ ID NO: 8), Y at position 46, a sequence present in the catalytic domain identified as a binding site for Grb2 via its SH2 domain.

Binding and inhibition of PTEN phosphatase may be assessed using recombinant wild type PTEN or mutants of PTEN and appropriate PIP$_3$ substrates to measure dephosphorylation of PIP$_3$ at D3 position. Agents which modulate PTEN phosphatase action should have efficacy in the treatment of cancer and inflammatory diseases. The dephosphorylation of phosphatidylinositol 3,4,5, -trisphosphate (PIP$_3$) is carried out in a reaction mixture consisting of 100 mM Tris-HCl (pH 8), 10 mM dithiothreitol, 0.5 mM diC$_{16}$ phosphatidylserine (PS), 25 uM PIP$_3$, diC$_{16}$, BIOMOL PH-107 (BIOMOL, Inc.) and 50 µg/ml purified recombinant PTEN. Lipids were prepared in organic solvents and dispensed into 1.5 ml microfuge tubes followed by solvent removal under reduced pressure. Buffer is then added and a lipid suspension is formed by sonication. PTEN phosphatase assays are initiated by the addition of PTEN and carried out at 37° C. At different time points, 15 µl of 100 µM NEM (N-ethylmaleimide) is added to 10 µl of reaction mixture followed by rapid centrifugation 18,000× g for 15 minutes at 4° C. Liberated inorganic phosphate is detected in twenty microliters of supernatant using the Malachite green assay and an inorganic phosphate standard curve. Malachite green reaction with inorganic phosphate is detected spectrophotometrically at 620 nm wavelength. The N terminal domain also contains the P-loop (HCKAGKGR, residues (123–130; SEQ ID NO: 9) which is unique to PTEN. Two basic residues, K125 and K128 at the active site likely account for the capacity of the P-loop to accommodate the large PIP$_3$ as a substrate. The cysteine residue at position 124 forms a thiophosphate intermediate with the phosphorylated PIP$_3$ molecule. R130 is involved in catalysis of this phosphoester linkage. The His at position 123 and Glycine at position 127 are also critical for the conformation of the P-loop structure. The trough region defined by the active site is extended to 8 angstroms in depth and 5×11 angstrom opening to the active site. This site will be targeted for molecular modeling to develop inhibitors specific for the PTEN phosphatase. Comparisons with other phosphatases (PTP and PTP1B) with PIP$_3$ activity will facilitate identification of those agents which specifically interact with PTEN.

The WPD loop or DHNPPQ motif (residues 92–97; SEQ ID NO: 10) is equally important in catalysis in that mutation of Asp-92 results in a loss of catalytic activity. This aspartic acid residue acts as a general acid to protonate the phenolic oxygen atom of a tyrosyl group for tyrosine phosphatases. These data suggest that the mechanistic action of PTEN is similar to that of tyrosine phosphatases during hydrolysis of the phosphate ester in PIP$_3$.

The invariant sequence in the WPD loop will also be used in a combinatorial drug screen based on the electrostatic charge characteristics of this region of the PTEN molecule. Functional side chains of these amino acids will be targeted with organic molecules which mimic or disrupt the WPD interaction with the P-loop and TI-loop residues. For these screens a PTEN inert organic scaffold will be developed to allow for detection of organic molecules which specifically bind PTEN or PTEN fragments.

The structure of the TI loop in the N terminal domain facilitates PTEN-mediated dephosphorylation of the $PIP_3$ molecule by providing an elongated and enlarged catalytic site. This is in contrast to other dual specificity phosphatases. Residues (164–174) in the T1 loop include KGVTIP-SQRRY; (SEQ ID NO: 17). These residues are 100% conserved. The serine residue at position 170, R at 173 and Y at 174 in this PTEN peptide are important in maintaining the interaction between the TI loop and the C2 domain and are often mutated in human tumors.

The TI loop of PTEN is in close proximity to the C2 domain and maintains a rigid interface to promote the open configuration for $PIP_3$ binding to PTEN. A 100% conserved region in C2 domain, HFWVNTFFI,(SEQ ID NO: 11) will also be used to screen a combinatorial library for organic molecules which bind to this motif.

Small molecules which have affinity for the C terminal tail of PTEN will also be screened and characterized. Molecules so identified should decrease degradation of PTEN in cells by interfering with phosphorylation of residues, S380, T382 and T383 within the sequence RYSDTTDS (SEQ ID NO:16) at the extreme C terminus. Screens will be performed with recombinant GST PTEN protein comprising the last 50 amino acids (residues 350–403) of PTEN to identify those agents which have affinity for this region of PTEN. This methodology should identify agents that will antagonize the phosphorylation of PTEN tail and/or interfere with PDZ binding thereby blocking PTEN interaction with the plasma membrane. Agents which disrupt this PDZ interaction will likely interfere with PTEN degradation and hence increase PTEN activity levels in vivo.

Another suitable target present in the C-terminal domain of PTEN is the PEST domain. This region encodes a site for ubiquitin mediated degradation of PTEN which, if blocked, should augment PTEN activity by preventing its degradation. Other sequences present in the C terminus of PTEN between residues 251–351 include TLTKNDLD-FTKTV (SEQ ID NO:12), GDIKVEF-FTKTV (SEQ ID NO:13), DKANKDKAN-FTKTV (SEQ ID NO:14).

The present invention is not only directed to methods for the rational design and screening of agents having binding affinity to the particular peptide sequences described above. Several PTEN mutants are disclosed herein which may also be used to advantage to identify molecules which modulate PTEN activity. For example, the C124S mutant of PTEN provides an ideal target for the initial screening of therapeutic agents given its increased affinity for substrates and substrate trapping capacity in vivo. Use of this mutant PTEN in the assays of the invention should result in the identification and characterization of phosphoinositol D3 analogs that inhibit PTEN activity. Such agents should include organic chemicals with the capacity to disrupt the vicinal sulfhydryl interaction of C124 with the phosphate group required to form a thiol-phosphate intermediate for cleavage of the inositol phosphate bond. Agents which so modulate action of the C124S mutant of PTEN will then be further assessed in functional phosphatase assays.

Monoclonal antibodies, proteins, protein fragments, peptides and peptidomimetic analogs of peptides which simulate the binding site for $PIP_3$ as well as structural homologs of phosphoinositides phosphorylated in D3 position, or substituted in the D3 position with other negatively charged functional groups, will be screened for capacity to bind and modulate PTEN phosphatase activity in vitro. Molecular modeling should facilitate the identification of specific organic molecules with capacity to bind to the active site of PTEN based on conformation or key amino acid residues required for catalytic function. A combinatorial chemistry approach will be used to identify molecules with greatest activity and then iterations of these molecules will be developed for further cycles of screening.

The PTEN polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a PTEN polypeptide or fragment and the agent being tested, or examine the degree to which the formation of a complex between a PTEN polypeptide or fragment and a known substrate is interfered with by the agent being tested.

Another technique for drug screening provides high throughput screening for compounds having suitable binding affinity to PTEN polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with PTEN polypeptide and washed. Bound PTEN polypeptide is then detected by methods well known in the art.

A further technique for drug screening involves the use of host eukaryotic cell lines or cells (such as described above) which have a nonfunctional PTEN gene. These host cell lines or cells are defective at the PTEN polypeptide level. The host cell lines or cells are grown in the presence of drug compound. The rate of cellular proliferation and transformation of the host cells is measured to determine if the compound is capable of regulating the proliferation and transformation of PTEN defective cells.

Another approach entails the use of phage display libraries engineered to express fragment of PTEN on the phage surface. Such libraries are then contacted with a combinatorial chemical library under conditions wherein binding affinity between the PTEN peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19–21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527–533). In addition, peptides (e.g., PTEN polypeptide) may be analyzed by an alanine scan (Wells, (1991) Meth. Enzym. 202:390–411). In this technique, an amino acid residue is replaced by Ala, and its effect on the peptide's activity is determined. Each of the amino acid residues of the peptide is analyzed in this manner to determine the important regions of the peptide. It is also possible to isolate a target-specific antibody, selected by a functional assay, and then to solve its crystal structure. In principle, this approach yields a pharmacore upon which subsequent drug design can be based.

It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved PTEN polypeptide activity or stability or which act as inhibitors, agonists, antagonists, etc. of PTEN polypeptide activity. By virtue of the availability of cloned PTEN sequences, sufficient amounts of the PTEN polypeptide may be made available to perform such analytical studies as x-ray crystallography. In addition, the knowledge of the PTEN protein sequence provided herein will guide those employing computer modeling techniques in place of, or in addition to x-ray crystallography.

Suitable peptide targets for identifying specific PTEN binding and modulating agents are provided in Table I B. Pharmaceuticals and Peptide Therapies The elucidation of the role played by PTEN in cellular transformation and angiogenesis facilitates the development of pharmaceutical compositions useful for treatment and diagnosis of PTEN associated disorders. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

C. Methods of Gene Therapy

As a further alternative, the nucleic acid encoding the authentic biologically active PTEN polypeptide could be used in a method of gene therapy, to treat a patient who is unable to synthesize the active "normal" polypeptide or

TABLE I

| PTEN peptide motifs used to screen for PTEN agonists and inhibitors | |
|---|---|
| Phosphorylation site motifs: | amino acid residue number |
| DLDLTYIYP | (22–30) SEQ ID NO: 3 |
| YLVLTL | (27–30) SEQ ID NO: 6 |
| YRNNIDD | (46–52) SEQ ID NO: 8 |
| KGVTIPSQRRYVYYYSYLL | (164–182) SEQ ID NO: 15 |
| YSYL | (178–181) SEQ ID NO: 7 |
| YFSPN | (336–339) SEQ ID NO: 5 |
| RYSDTTDS | (378–385) SEQ ID NO: 16 |
| Catalytic Domain motifs | (1–185) |
| HCKAGKGR (P-loop) | (123–130) SEQ ID NO: 9 |
| DHNPPQ (WPD-loop) | (92–97) SEQ ID NO: 10 |
| KGVTIPSQRRY (TI-loop) | (164–174) SEQ ID NO: 17 |
| C2 domain motifs | (186–350) |
| HFWVNTFFI | (272–280) SEQ ID NO: 11 |
| C terminal tail related regions of interest | (351–403) |
| TLTKNDLD---FTKTV (PEST domain sequences) | (319–351) SEQ ID NO: 12 |
| GDIKVEF---FTKTV (PEST domain sequences) | (251–351) SEQ ID NO: 13 |
| DKANKDKAN---FTKTV (PEST) | (331–351) SEQ ID NO: 14 |
| RYSDTTDS (pre-PDZ region) | (378–385) SEQ ID NO: 16 |
| HTQITKV (PDZ-MAGI-2 interaction domain) | (399–403) SEQ ID NO: 18 | unable to synthesize it at the normal level, thereby providing the effect elicited by wild-type PTEN and suppressing the occurrence of "abnormal" PTEN associated diseases such as cancer.

Vectors, such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses.

Gene transfer techniques which selectively target the PTEN nucleic acid to malignant tissues are preferred. Examples of this include receptor-mediated gene transfer, in which the nucleic acid is linked to a protein ligand via polylysine, with the ligand being specific for a receptor present on the surface of the target cells. Microcapsule based delivery systems are also available for delivery of nucleic acids to targeted cell types.

The following Examples are provided to describe the invention in further detail. The Examples are intended to illustrate and not to limit the invention.

EXAMPLE 1

Orthotopic Brain Tumor Model

To determine whether PTEN exerts control over angiogenesis and/or the growth of glial tumors, an orthotopic brain tumor model was developed in which PTEN-deficient tumor cells were genetically manipulated in vitro and then stereotactically injected into the frontal cerebral cortex of nude mice. The U87MG cell line employed in these studies is derived from a patient diagnosed with glioblastoma multiforme, a highly malignant and uniformly fatal brain tumor. This tumor and other human glioblastomas and glioblastoma cell lines contain a mutation in both PTEN alleles (U87MG cells have a homozygous mutation in PTEN resulting in a null genotype).

In the orthotopic brain tumor model, 100% of mice implanted intracranially with the parental U87 cells display a highly invasive and angiogenic pattern of brain tumor growth that results in mortality within 25–27 days. In view of these observations, the effect of reconstituting expression of the PTEN gene in the parental U87MG (U87) cell line was explored.

Stable derivatives of the parental U87 cells were generated following transduction with retroviruses encoding cDNA for wild type PTEN or specific mutants of this phosphatase. In particular, missense mutations in the PTP signature motif were introduced to ascertain the importance of the enzymatic activity of PTEN to its tumor suppressor function. Missense mutations included the G129E mutant, which displays a severely attenuated ability to dephosphorylate inositol phospholipids, but retains normal enzymatic activity for phosphoproteins. The biological significance of the G129E mutant was underscored by the fact that its presence has been correlated with Cowden's disease and endometrial cancer. In another missense mutation generated, the R130M mutant, all phosphatase activity has been abrogated (Myers et al PNAS 1997, Funari et al PNAS 1997).

Figure 1B:
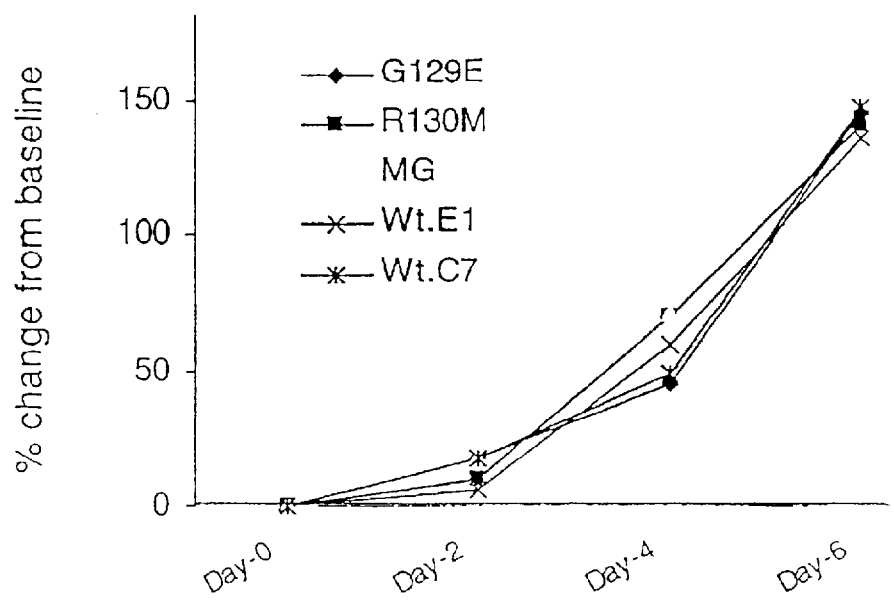

Tumor cells were characterized biochemically for levels of activated AKT (phospho-S473-AKT), growth in vitro and PTEN expression (FIG. 1). Anti-PTEN blots confirmed that parental U87 cells did not express PTEN and that following reconstitution of PTEN expression, U87 cells expressed significant and comparable amounts of the wild type or mutant phosphatase protein. Expression of wild type PTEN, at levels similar to those observed in a mouse brain lysate, suppressed the activated state of AKT observed in PTEN-deficient U87 cells (FIG. 1A, lanes 3 & 5). Following expression of the R130M and G129E mutant forms of PTEN, the levels of phospho-AKT were similar to those observed in the parental U87 cells (FIG. 1A, lanes 1, 2 & 4), suggesting that the lipid phosphatase activity of PTEN was essential for the effects on the PIP3-dependent activation of AKT. Interestingly, the growth of the different PTEN-expressing U87 cell lines in vitro was similar in 2, 5 and 10% fetal bovine serum (data not shown and FIG. 1B). Therefore, we compared these cell lines further in our in vivo models.

Figure 2A:
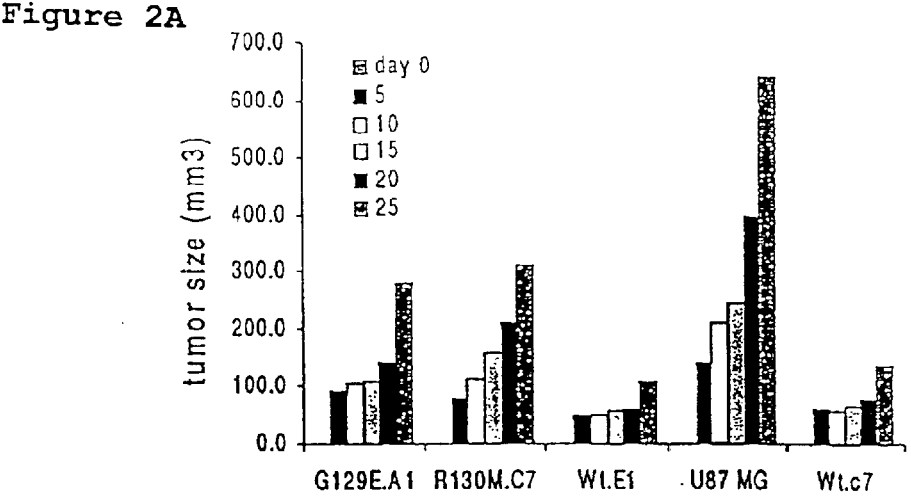
FIGS. 2A, 2B and 2C present data showing the effects of PTEN on growth of U87MG cells in vivo.
Figure 2B:
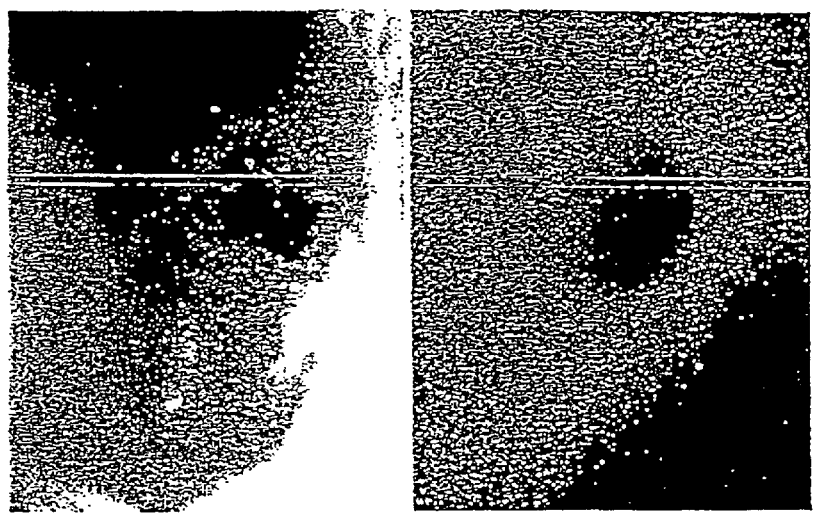
Figure 2C:
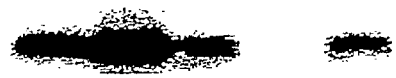
Figure 2C:
Figure 2C:
Figures 3A, 3B, 3C:
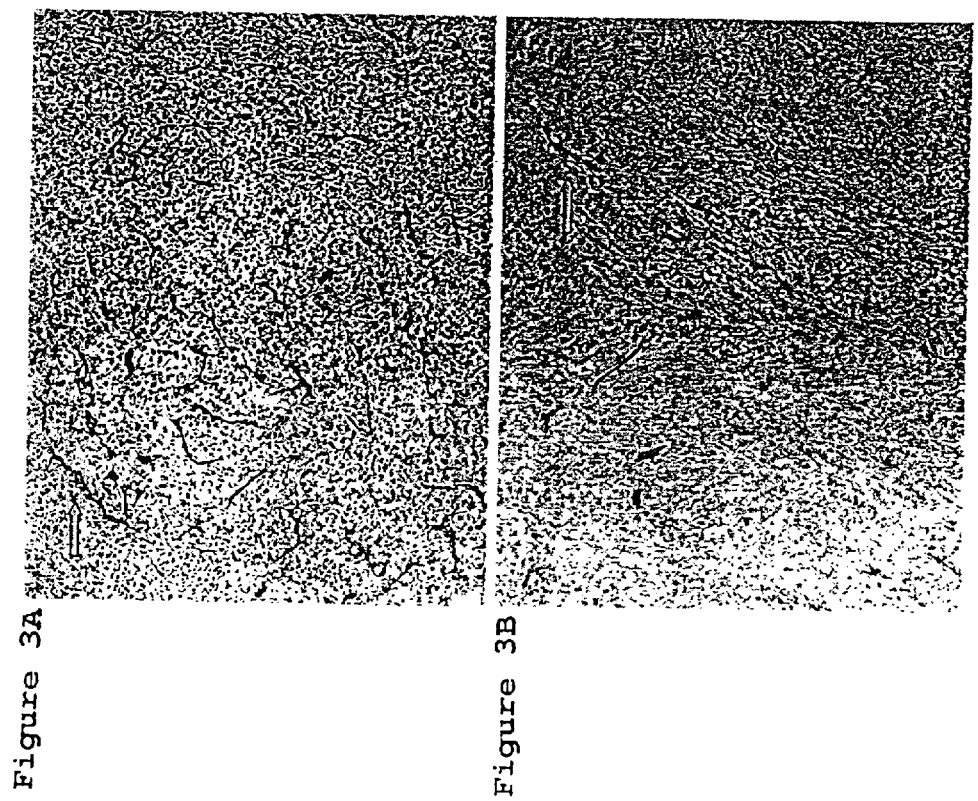
FIGS. 3A–3E show that PTEN suppresses angiogenesis. Immunohistochemical analysis of staining with CD31 antibody to evaluate the angiogenesis response within the parental U87MG tumor (FIG. 3A) and PTEN reconstituted tumors (FIG. 3B) implanted into the subcutaneous tissue. In PTEN minus and tumors expressing mutants of PTEN, there are more new vessels formed (angiogenesis) (upper panel, arrow indicated) than in wild-type PTEN reconstituted tumor (lower panel), indicating the PTEN has direct influence on angiogenesis during tumor growth.

Athymic nude mice were implanted subcutaneously and by intracranial injection. Production of subcutaneous tumors facilitates monitoring of tumor size and performance of direct biochemical analysis of tumor tissue for the examination PTEN expression and levels of AKT activation without significant contamination from other tissues. Tumor tissue blocks were processed for H & E staining, which confirmed that >95% of the tissue examined comprised tumor cells free of dermal or subdermal tissue. The levels of PTEN in tumor tissue and numerous normal tissues within the athymic nude mouse were compared. Using anti-PTEN antisera, the expression of PTEN was detected in all tissues, with the exception of skeletal and heart muscle (data not shown). No PTEN was detected in parental U87-derived tumor tissue (FIG. 2C, lane 4). These results demonstrate that the tumor tissue sampled contained predominantly tumor cell-derived proteins. As observed in the cell lines grown in vitro, subcutaneous tumors derived from U87 cells reconstituted with mutant or wild type PTEN display similar levels of PTEN expression (FIG. 2C, lanes 1, 2, 3 & 5). Phospho-AKT activity was higher in PTEN-null U87 cells and U87 cells reconstituted with R130M and to a lesser extent in U87 cells expressing the G129E mutant (FIG. 2C, lane 1) as compared to the wild type PTEN transduced cells (FIG. 2C, compare lanes 1, 2 & 4 to lanes 3 & 5). The pattern of phosphorylated AKT was similar when the different U87 mutant expressing cell lines were assayed in vitro or in vivo (compare FIGS. 1A to 2C). Despite the similar in vitro growth rate, there was a dramatic difference in the growth of tumors derived from parental U87 cells compared to cells reconstituted with wild type PTEN (FIGS. 2A & B). The average volume of U87-derived tumors on day 25 after implantation was 848±203 mm3, compared to 91±27 mm3 for tumors derived from PTEN-reconstituted cells (n=5, p<0.0001). Reconstitution with catalytically dead mutants of PTEN significantly reduced the rate of growth in vivo without a demonstrable effect on angiogenesis (FIGS. 2A and 3C). Others have observed effects of catalytically dead PTEN expression on cell invasion, suggesting a function for other regions of the PTEN molecule in cellular functions. Interestingly, in vivo BrdU labeling of tumor cells revealed no significant difference in number of cells in S phase (72±6 BrdU positive cells per field in parental U87MG tumor mass versus 68.5±3 in WT PTEN reconstituted tumors). These data demonstrated that the loss of PTEN-mediated inositol phospholipid phosphatase activity was a critical component of deregulated tumor growth. Notably, the G129E mutant (which lacks inositol phospholipid phosphatase activity) was equivalent to the R130M mutant (which lacked inositol phospholipid and phosphoprotein activity) with respect to both tumor growth and the proliferative rate of these tumors in vivo.

To assess the effect of PTEN on angiogenesis, parental U87 cells were compared to cells reconstituted with wild type or mutant PTEN. Cryostat sections from subcutaneous tumors for were stained for CD31 (PECAM), an endothelial marker used to measure the microvessel density of these tumors. Microvessel density was assessed from multiple digitized images of CD31-stained tumor tissue at 100× magnification (3 fields were evaluated per tumor) and counted blindly for the number of CD31 positive microvessels per unit surface area as described (Weidner et al 1991 N Engl J Med 324:1–8). Reconstitution of PTEN expression in U87 cells dramatically suppressed the angiogenic response in vivo (FIGS. 3A & B). Quantitation of microvessel density in tumors derived from parental U87 cells (77±13) and U87 cells expressing wild type PTEN (38±7) revealed an 50% suppression of angiogenesis (FIG. 3C) (n=5, p<0.001). The microvessel density of tumors derived from U87 cells reconstituted with catalytically impaired PTEN (R130M, 84±15 or G129E, 69±16) were not significantly different (p>0.05) from the parental U87 cell line (FIG. 3C). Similar results were obtained from an analysis of microvessel density of intracranial tumors. The levels of phospho-AKT detected within the tumor mass in vivo demonstrated a mechanistic link between the loss of the inositol lipid phosphatase function of PTEN, the phosphorylation status AKT and the angiogenic phenotype within the tumor.

Figure 3D:
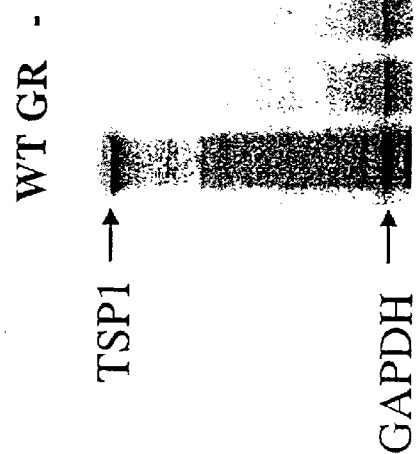
Figure 3E:
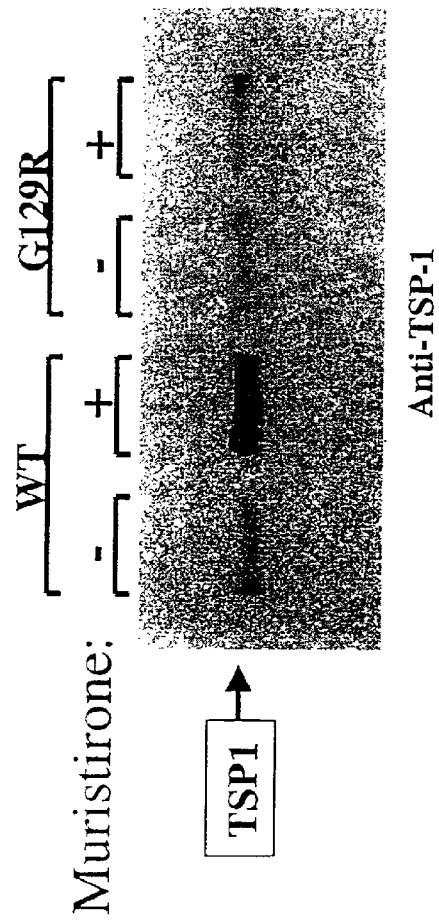

Recent in vitro data suggested a link between PTEN and downstream targets including AKT, HIF1α and VEGF in the potential control of angiogenesis (Zundel et al., Genes Dev 2000, Zhong et al., Cancer Res 2000). We used the RNase protection assay (RPA) to examine the effect of PTEN on thrombospondin 1 (TSP-1) expression. RPA was performed with a TSP-1 specific probe in U87MG cells constitutively expressing wild type PTEN or G129R PTEN (FIG. 3D). The data demonstrate that wild type but not mutant PTEN expression induces TSP-1 in U87 cells. To confirm these results, Western blot analysis was performed to assess TSP-1 expression in a retroviral-based ecdysone-inducible PTEN expression system (No et al PNAS 1996). Inducible and dose-dependent expression of PTEN was confirmed in U87 cells. The induced expression of wild type PTEN, but not G129R PTEN, resulted in augmentation of thrombospondin 1 expression (FIG. 3E) and suppression of AKT activation as demonstrated by decreased phospho-AKT levels without an accompanying decrease in total AKT (data not shown). The induced expression of mutant G129R had no effect on phospho-AKT levels. The data therefore demonstrate that PTEN positively modulated the expression of thrombospondin 1, a negative regulator of angiogenesis (FIGS. 3D and E) (Sheibani and Frazier, (1999) Histol. Histopathol. 14:285–294, Hsu et al., (1996) Cancer Res. 56:5684–5691). These data suggested that PTEN has a pivotal role in angiogenesis mediated, in part, by the induction of TSP-1.

Vascular endothelial growth factor (VEGF) is a known positive regulator of angiogenesis (Jiang et al. (2000) Proc Natl Acad Sci USA, 97(4), 1749–53; Mazure et al. (1997) Blood, 90(9), 3322–31; Mazure et al. (1996) Cancer Res, 56(15), 3436–40; Plate et al. (1994) Int J Cancer, 59(4), 520–9; Plate et al. (1992) Nature, 359(6398), 845–8). The capacity of tumor tissue to produce VEGF was determined for U87MG parental cells null for PTEN versus U87 cells reconstituted with wild type PTEN or mutants of PTEN (G129E or R130M). Tumor tissue obtained from subcutaneously implanted tumor cells was subjected to cryostat sectioning and multiple sections through the tumor tissue were pooled for biochemical Western blot analysis using anti-VEGF antibody (Santa Cruz, SC-507). Cell lysates were assayed for protein concentration by Bradford method. Equivalent amounts of total protein were resolved by SDS PAGE followed by immunoblot for VEGF protein.

Figure 4:
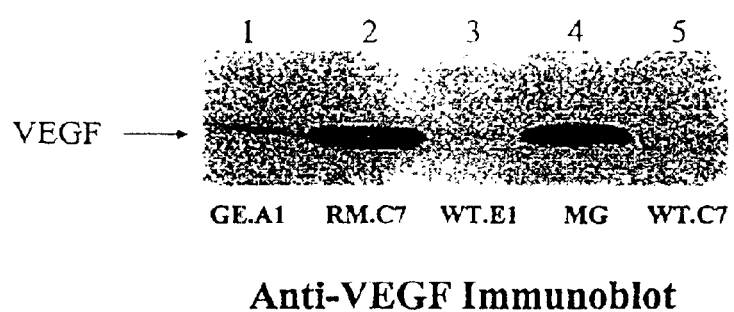
FIG. 4 is a Western blot showing the effect of constitutive PTEN reconstitution on VEGF expression in U87MG cells. VEGF immunoblot analysis of parental U87MG or PTEN wild type or mutant reconstituted tumor cell lysates revealed a dramatic suppression of VEGF in wild type and G129E mutant PTEN reconstituted tumor cells.

The results demonstrate that the reconstitution of wild type PTEN but not catalytically dead PTEN markedly suppresses the production of VEGF by U87MG tumors in vivo. No VEGF was detected in tumors reconstituted with the wild type PTEN (FIG. 4, lanes 3 and 4). An intermediate level of suppression is noted in tumors reconstituted with the G129E mutant of PTEN (FIG. 4, lane 1), a mutant which has lost its capacity to dephosphorylate $PIP_3$ and not protein substrates. These data show the first evidence that PTEN suppresses VEGF, a proangiogenic growth factor in vivo. The data implicate PTEN and therefore, the PI-3 kinase cascade in the coordinate regulation of the "angiogenic switch" mechanism which controls angiogenesis under normal physiologic conditions. It is this control that is lost during tumor progression.

Figure 5A:
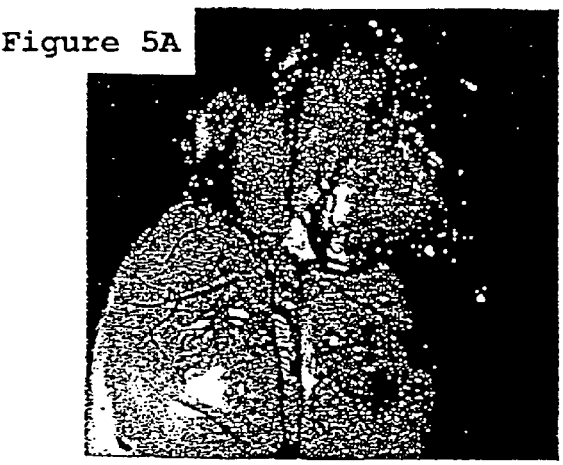
FIGS. 5A–E are a series of micrographs and a graph showing the effects of PTEN reconstitution on survival in an orthotopic brain tumor model. Equivalent number of parental U87 cells or U87 cells reconstituted with wild type or mutant alleles of PTEN (see legend)(1×106 cells) were implanted in right frontal lobe of nude mice. Stereophotography of whole brains from mice implanted with U87MG tumor cells (day 25) (FIG. 5A), or PTEN reconstituted (day 42) (FIG. 5B). The implantation site is shown by position of arrow in the wild type PTEN reconstituted tumor, (FIG. 5C) A R130M PTEN reconstituted tumor implanted into a nude mouse brain (magnification ×20).
Figure 5B:
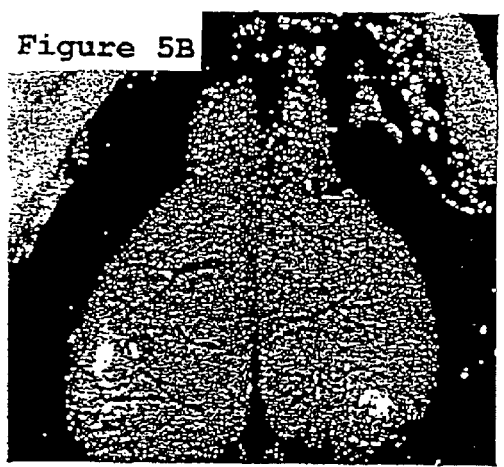
Figure 5C:
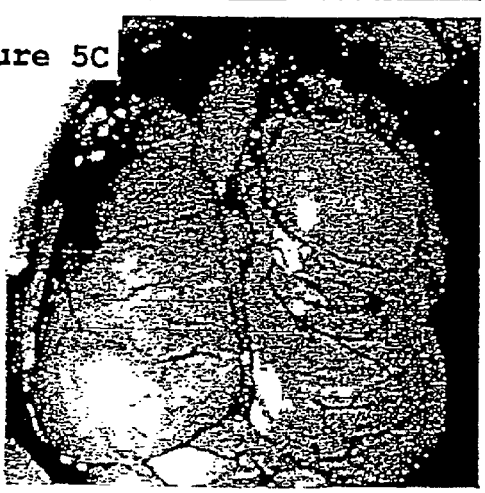
Figure 5D:
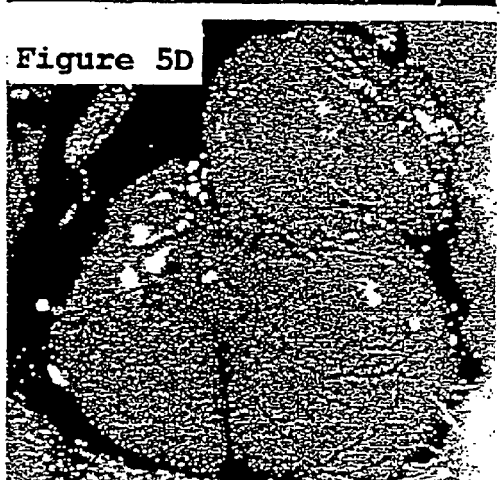
Figure 5E:
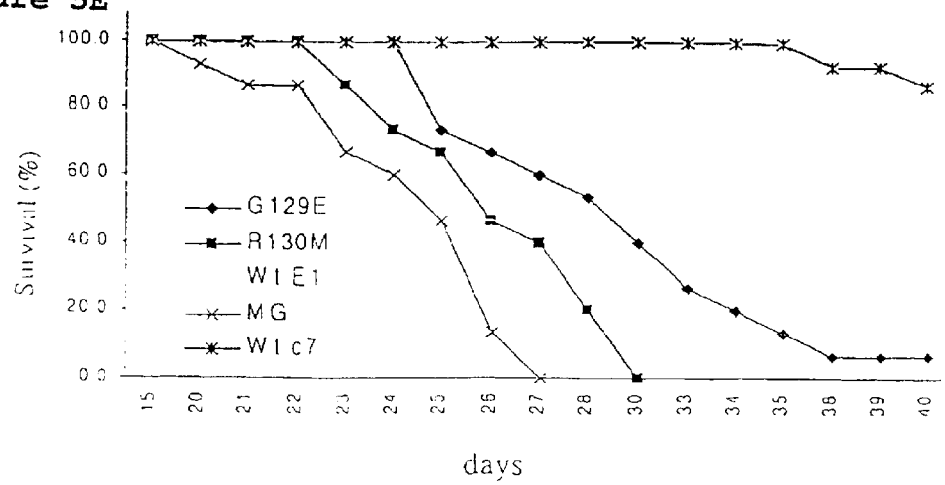

Brain tumor-induced angiogenic responses are known to occur in the context of brain specific stromal and extracellular matrix interactions. To determine whether the expression of PTEN affected the survival of mice in an orthotopic brain tumor model, U87 cells expressing either wild type or mutant forms of PTEN were implanted under stereotactic control into the right frontal lobe of nude mice (FIGS. 5A–D, see arrow for site of implantation). The results demonstrated that reconstitution of wild type PTEN in U87 cells suppressed the malignant potential of these cells in an orthotopic animal model. Thus, there was 90% survival at 40 days in animals implanted with the wild type PTEN-reconstituted U87 cells compared to 100% mortality of mice implanted with the parental cells at 27 days (FIG. 5E) (n=15, p<0.0001). PTEN reconstituted tumor cells grew more slowly when implanted in the frontal lobe (FIG. 5, compare A & B) and remained circumscribed to that area of brain (data not shown). U87 cells reconstituted with PTEN mutants, ablated for either inositol lipid phosphatase activity (G129E) or all phosphatase activity (R130M), displayed a phenotype similar to the PTEN-negative, parental U87 cells (FIG. 5C). Animals with tumors derived from U87 cells reconstituted with PTEN-G129E displayed slightly prolonged survival (50% at day 30) compared to those implanted with parental U87 cells; all of these animals were dead, however, by day 40. These data implicate the inositol lipid phosphatase activity of PTEN is required for controled angiogenesis (FIG. 3) and its loss is correlated with the development of a highly malignant glioma (FIG. 5C) following implantation of U87 tumor cells in mice.

EXAMPLE II

PTEN Reconstitution Reduces Metastatic Potential of Brain Tumor Cells Introduced via the Carotid Artery and Negatively Regulates Proangiogenic Factors The following methods are provided to facilitate the practice of Example II.

As described in Example I, wild type PTEN or mutant PTEN (G129E, R130M) cDNAs were subcloned into the pBabe-puro retroviral expression vector. Stable clones of U87MG cells were established under puromycin selection (2 ug/ml) (Myers et al. 1998). A panel of antibodies were obtained which are immunospecific for PTEN (Myers et al. 1998), AKT, phospho-AKT (New England Biolabs, #9270), TIMP-3, MMP-9, and MMP-2 (Sigma).

To evaluate the role PTEN plays in regulating the expression of factors that promote angiogenesis and invasiveness of glial tumors, an in vitro gelatin zymography assay was performed. Gelatin zymography specifically detects the presence of members of the matrix metalloproteinase (MMP) family of proteins, which degrade the ECM, thereby promoting angiogenesis and metastasis. The assay was performed using either 1) lysates derived from tumor tissue or 2) conditioned media in which the tumor cells or tissue were maintained. Protein samples for analysis were generated from isolated subcutaneous tumors by dissolving the tumor tissue in a detergent lysis buffer [50 mM Tris-Cl, (pH 8.0), 150 mM NaCl, 0.05% NP-40, 100 mM NaF, 1 mM EDTA, 1 mM EGTA, 0.08 mM PMSF, 0.01 mg/ml leupeptin, 0.01 mg/ml aprotinin, 1 $\mu$mg/ml pepstatin A]. Protein samples for analysis were also generated from tumor cell conditioned media concentrated by centrifugation through Microcon® YM-10 centrifugal filter devices. The protein concentration of samples composed of either tumor cell lysate or concentrated, conditioned media derived from the various tumor cell cultures was determined by standard protein assay (Bio-Rad, Hercules, Calif.). Protein samples were then normalized for equal protein concentrations.

Protein samples (10 $\mu$g) were subjected to substrate gel electrophoresis with modifications. Briefly, protein samples normalized for protein concentration were applied, under non-reducing conditions, to 10% polyacrylamide slab gels impregnated with 1 mg/ml gelatin (DIFCO). After electrophoresis, the gel was washed at room temperature for 30 minutes in washing buffer [50 mM Tris-Cl (pH 7.5),5 mM $CaCl_2$, 1 mM $ZnCl_2$, 2.5% Triton X-100] and then incubated overnight at 37° C., with gentle agitation, in washing buffer containing 1% Triton X-100. The gels were stained with a solution of 0.1% Coomassie brilliant Blue R-250. Clear zones in the gel are indicative of the presence of gelatinolytic activity contained in a given protein sample. The gelatinolytic activity was quantitated by densitometric scanning and analysis.

To further evaluate the role PTEN plays in regulating the expression of factors that promote angiogenesis and invasiveness of glial tumors, Matrigel® invasion assays were also performed. Matrigel® invasion assays are a standard procedure used to characterize the metastatic potential of cells, based on the ability of such cells to degrade the Matrigel® extracellular matrix (ECM). Matrigel® is a commercially available mix of basement membrane components, generated from an EFS sarcoma, which includes basic components of the basement membrane such as collagens, laminin, and proteoglycans, as well as matrix degrading enzymes, their inhibitors, and growth factors. Invasion of tumor cells into Matrigel® has been used to characterize involvement of matrix-degrading enzymes which play important roles in tumor progression and metastasis (Benelli and Albini, 1999).

The assay was performed as follows: Matrigel® (Becton-Dickinson) was thawed overnight at 4° C. on ice and diluted to 1 mg/ml in serum-free DMEM. 50 $\mu$l of the diluted Matrigel® was added to the upper chambers of a 24-well Transwell® plate(0.8 $\mu$m pore size, Costar). The upper chambers were then incubated at 37° C. for 6 hours to facilitate solidification of the gelatinous matrix. U87 glioma cells were harvested from tissue culture flasks by 0.04% Trypsin/EDTA and washed three times with serum-free DMEM to remove trace amounts of sera. Cells were resuspended in serum-free DMEM at a density of $5 \times 10^5$ cells/ml, 200 $\mu$l of which was added to upper chambers coated with solidified Matrigel®. The lower chambers of the Transwell® plate were filled with 600 $\mu$l of DMEM containing 5 $\mu$g/ml fibronectin, which served as a soluble attractant and adhesive substrate. Transwell® plates were incubated at 37° C. for 36 hours to facilitate migration of U87 cells from the upper chambers into which they were seeded to the lower chambers. Following this incubation time, the upper chambers were removed and stained with 0.1% crystal violet solution to visualize the cells. Cells that failed to migrate to the underside of the porous membrane that separates the top and bottom chambers of the Transwell® were removed by scraping the topside of the membrane with a cotton-tipped swab. Cells that had successfully migrated through the Matrigel® to the underside of the porous membrane were characterized as invasive cells and counted under 100× magnification.

An in vivo study of experimental metastasis following orthotopic introduction U87 glioma cells into the nude mouse brain was also undertaken. U87MG cells were introduced into the circulatory system of a mouse via the injection of cells into the intracarotid artery. Each mouse was anesthetized by intraperitoneal injection of Nembutal and restrained on a cork board equipped with fixed rubber bands that were used to wrap around the teeth of the upper jaw, thereby immobilizing the head. Under a dissecting microscope, the hair over the trachea (if a mouse species having hair was used) was shaved, the neck was prepared for surgery with betadine, and the skin cut by a mediolateral incision. After blunt dissection, the trachea was exposed and the muscles separated to expose the right common carotid artery, which was then separated from the vagal nerve. Further dissection was then performed to reveal the internal and external carotid arteries. The common carotid artery was prepared for injection distal to the point of division between the internal and external carotid arteries. Briefly, a ligature of 5–0 silk suture was placed in the distal portion of the common carotid artery and a second ligature was positioned and tied loosely proximal to the injection site of the internal carotid artery. A sterile cotton tip applicator was inserted under the artery just distal to the injection site to elevate the artery. This procedure controlled bleeding from the carotid artery by regurgitation from distal vessels. The artery was nicked with a pair of microscissors, and a plastic cannula (<30 gauge) was inserted into the lumen and threaded forward into the internal carotid artery. Wild type cells or cells expressing the various mutants of PTEN, G129R, G129E, R130M, ($1 \times 10^6$ in 10 $\mu$l) resuspended in PBS were injected slowly into the artery, after which the cannula was removed. The second ligature was then tightened and the incision in the skin sealed with surgical clips.

Following completion of the surgery, mice were placed in clean cages equipped with heating sources to maintain their body temperature. The mice were then monitored until they recovered from the effects of the anesthesia and returned to the care of the animal facility. Deleterious systemic effects associated with brain lesions, such as cachexia, listlessness, and protrusion of the right bulb were monitored. Mice were sacrificed when moribund. Brains were removed and fixed in 10% formaldehyde for H&E staining and in OCT for frozen sections.

Cell lysates obtained from U87 cells grown in tissue culture or from multiple cryostat sections of U87MG subcutaneous tumor tissues were also run on gels and analyzed by Western blotting. A Bradford assay was performed to determine protein concentration of each lysate. Equivalent amounts of protein were resolved by SDS PAGE and transferred to nitrocellulose. Membranes were probed with antisera specific for PTEN, AKT, phospho-AKT or TIMP-3. The RNAase protection assay (RPA) was performed using a RPA III kit from (Ambion) according to the manufacture specifications. Briefly, 20 $\mu$g of total RNA was precipitated and resuspended in 10 $\mu$l of hybridization buffer containing specific radioactive probe. The RNA was then heated to 95° C. for 10 min and hybridized for 16 hours at 42° C. 150 $\mu$l of this mixture was treated with 1:100 dilution of RNAase in RNAase buffer for 30 minutes. The RNAase was inactivated and the RNA was reprecipitated and resolved on 5% acrylamide gel. RNA probes were synthesized using MAXI Script utilizing PCR templates and T7 polymerase. The GAPDH probe was provided in the kit as an internal control. The TIMP-3 probe represented a 590 nucleotide sequence located in the 3' UTR of the TIMP-3 sequence. All probes were sequenced.

Microvessel density (MVD) was determined for each brain tumor as described in Example I by CD31 staining, performed on cryostat sections (7 $\mu$m), fixed in acetone, blocked in 1% goat serum and stained with anti-CD31 antibody (Pharmingen, #01951D). Antibody staining was visualized with peroxidase-conjugated anti-mouse antibody and counter stained with hematoxylin. A negative control was performed on each tumor tissue stained with mouse IgG. Two sections from each tumor were scanned under low power magnification (40×) to identify areas of highest CD31 positive vessel density (Weidner et al. 1991), followed by digitization of 5 fields from this area. The digitized images representing one 100× field were counted for the number of CD31 positive vascular elements. Data was collected independently by two researchers in a blind study. The average number of microvessels per digitized 100× field was determined for 5 tumors per experimental group and analyzed by Student's t-test.

Figure 6:
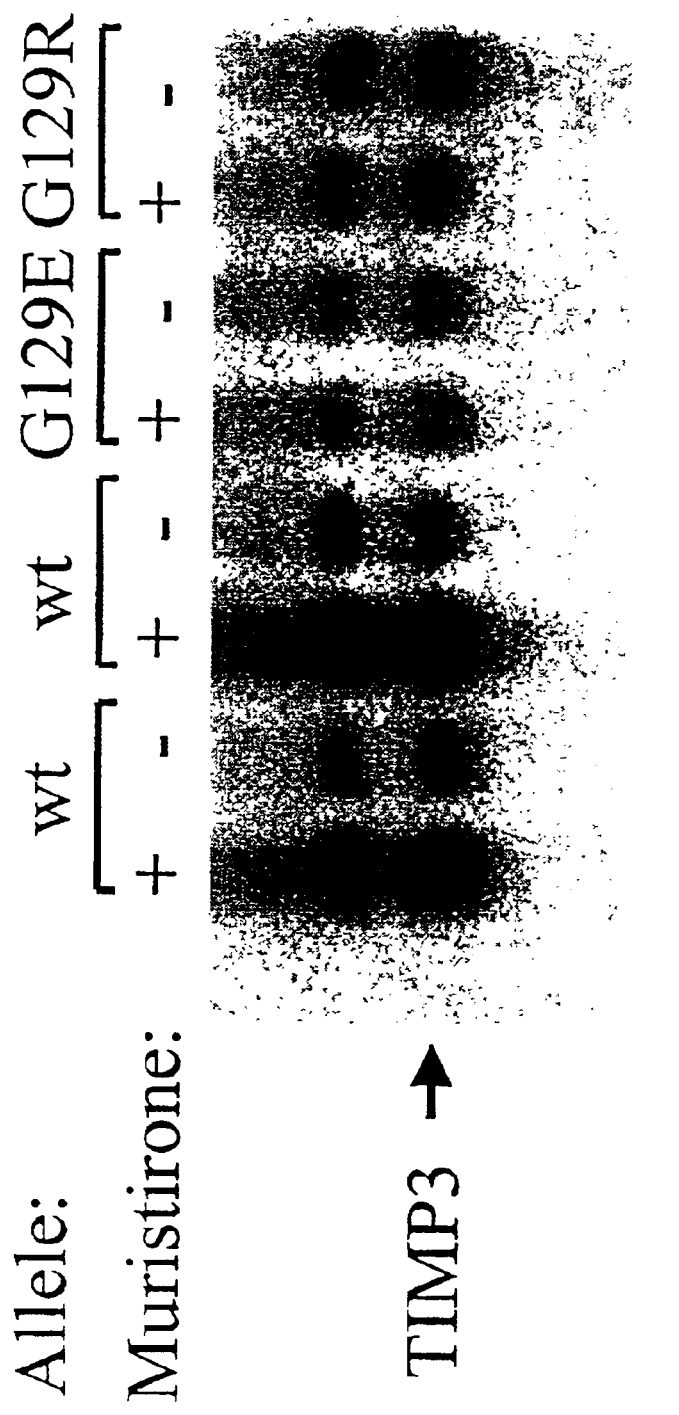
FIG. 6 is a blot showing that PTEN induces the expression of TIMP-3. PTEN regulates the expression of tissue inhibitor of metalloproteinase (TIMP-3) in U87MG cells. RNAase protection assay was used to measure levels of TIMP-3 mRNA in wild type PTEN expressing U87 cells or cells transduced with a mutant catalytically dead PTEN (G129R). U87MG cells were infected with retrovirus encoding wild type PTEN (WT), the catalytically dead, G129R mutant (GR) or empty vector retrovirus (−) and selected for 10 days in puromycin. RNA was harvested and RNAase protection assays were carried out using probes for TIMP-3 and GAPDH. A probe for glyceraldehyde phosphate dehydrogenase (GAPDH) was used as a normalization control.
Figure 7:
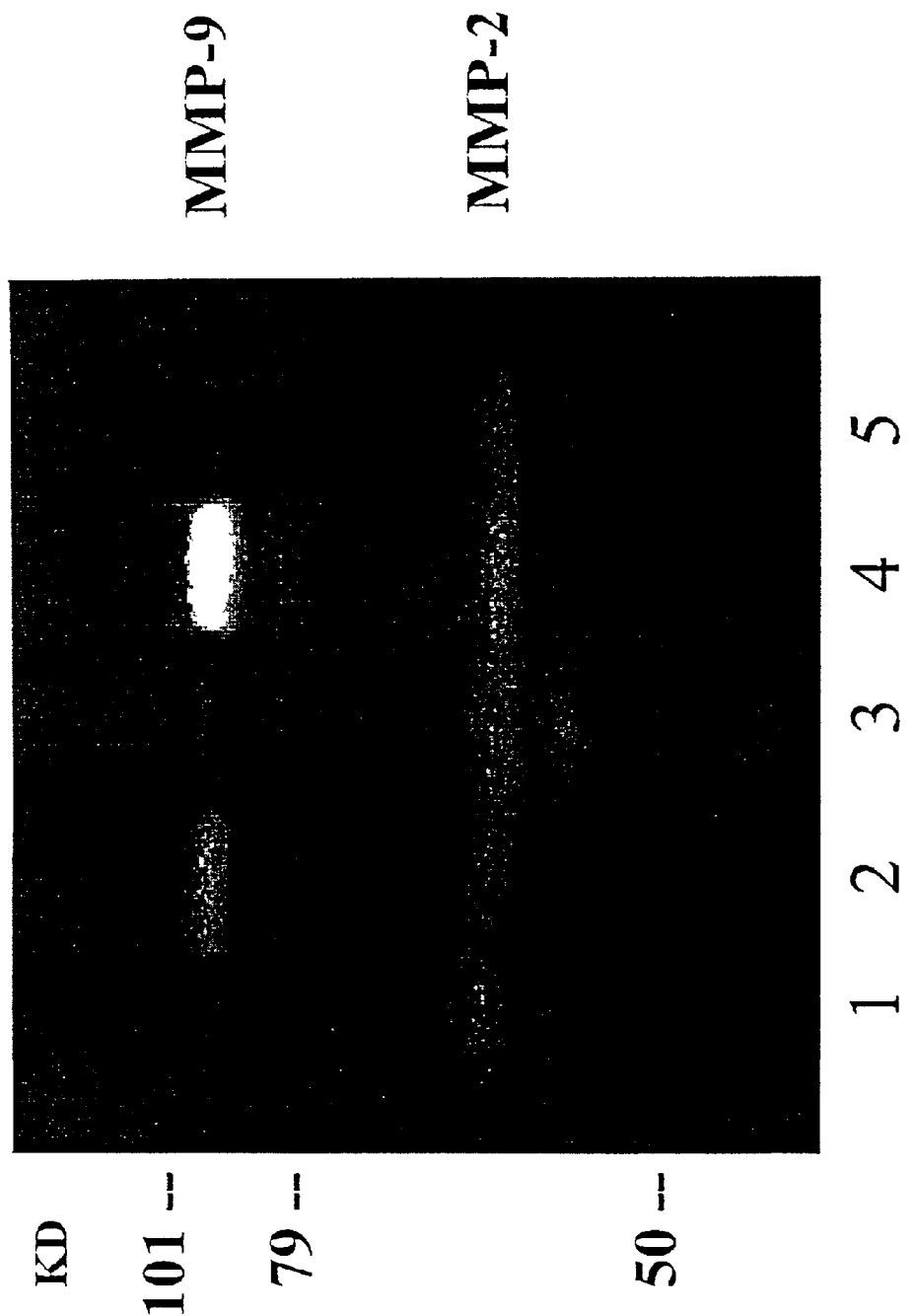
FIG. 7 is a gel showing that PTEN suppresses MMP-9 collagenolytic activity in vivo. Reverse zymography was used to evaluate the effect of PTEN reconstitution on collagenolytic activity within tumor tissue. The enzymatic activities of MMP-2 and MMP-9 were detected based on molecular weight and Western blot analysis (data not shown).

The data obtained thus far indicated that the antiangiogenic activity of PTEN can be correlated matrix remodeling and degradation. We used the RNAase protection assay (RPA) to confirm the effect of PTEN on TIMP-3 expression. RPA was performed with a TIMP-3 specific probe in U87MG cells constitutively expressing wild type PTEN or G129R PTEN. The data demonstrated that wild type, but not mutant PTEN expression induced TIMP-3 expression in U87 cells. Thus, PTEN positively modulates the expression of TIMP-3, a negative regulator of matrix metalloproteinases (FIG. 6). These data reveal a novel mechanism through which PTEN regulates angiogenesis and extracellular matrix remodeling via the induction of TIMP-3 and suppression of matrix metalloproteinase levels. To confirm this observation, matrix metalloproteinase activity in PTEN null and wild type PTEN reconstituted tumors (FIG. 7), was examined by performing reverse zymography for collagenolytic activity. Consistent with the finding that PTEN induced TIMP-3 expression in U87 tumor cells, it was apparent that wild type PTEN reconstitution suppressed MMP-9 activity with no effect upon MMP-2 activity (FIG. 7) (Oh et al. 1999; Rao et al. 1994).

Figure 8:
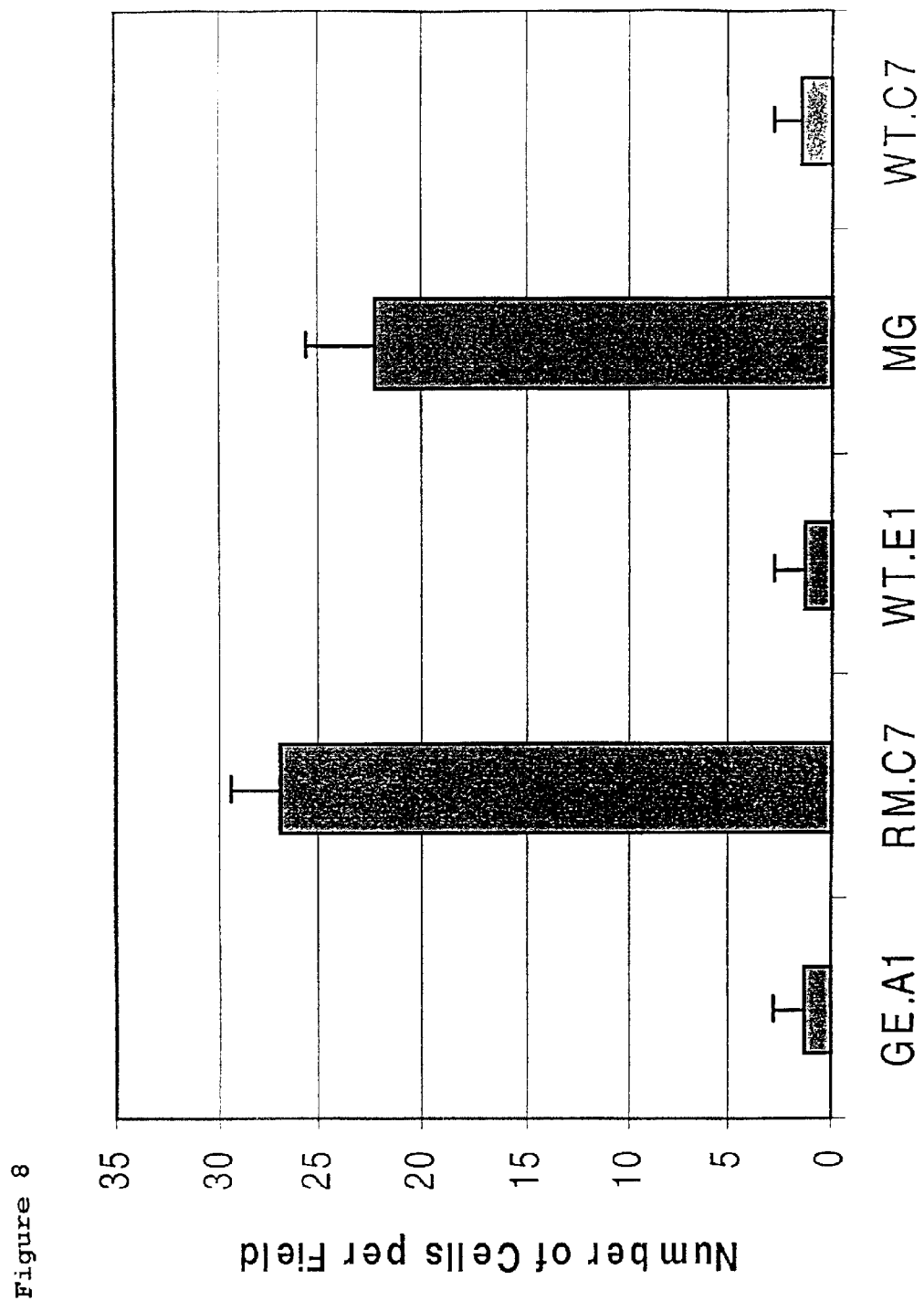
FIG. 8 is a graph showing the effects of PTEN reconstitution on tumor invasion. Equivalent numbers of parental U87 cells or U87 cells reconstituted with wild type or mutant forms PTEN. A transwell system coated with Matrigel (10 ug/ml) was used to assess the invasive properties of U87 cells versus PTEN reconstituted U87 cells in vitro. These data demonstrated that PTEN regulates the capacity of tumor cells to invade a complex matrix barrier.

To determine the role PTEN play is tumor cell invasion, PTEN deficient and PTEN reconstituted glioma cells were evaluated for their capacity to invade and migrate through a matrigel coated membrane. PTEN reconstitution was observed to completely abrogate invasion of U87 tumor cells through matrigel (FIG. 8). Adhesion and migration on matrigel remained intact in PTEN reconstituted U87MG cells (data not shown). Importantly, the data provided the first direct evidence that PTEN controls matrix degradation and the invasive behavior of tumor cells in vivo, and suggest that PTEN as well as PI-3 kinase inhibitors will suppress tumor invasion and the metastatic phenotype in vivo.

The data described above clearly demonstrate that mutations in the PTEN tumor suppressor in U87 glioblastoma cells resulted in the loss of normal physiologic control of matrix remodeling and invasion. Furthermore, analysis of the data revealed that PTEN exerts its effect at the level of TIMP-3 expression and control of MMP-9 matrix metalloproteinase activity. The results, therefore, implicate PI-3 kinase and other downstream targets of PTEN such as AKT, in the control of metastasis and invasion of tumor cells. The U87 brain tumor model therefore provides an ideal assay system to identify agents that negatively and/or positively regulate the activities of PTEN or other signaling molecules in the pathway such as VEGF, or bFGF, etc. which control matrix degradation in vivo. Finally, the results provided the first direct evidence that PTEN controls the capacity of a tumor to degrade the extracellular matrix in vivo. As mentioned previously, PTEN possesses lipid phosphatase activity which preferentially dephosphorylates phosphoinositides at the D3 position of the inositol ring. To date, PTEN is only one of two enzymes reported to have this activity. Reconstitution of PTEN in tumor cells that carry mutations in the PTEN gene, have established that this phosphatase regulates the PI-3 kinase-dependent activation of AKT, a major player in cell survival. This observation indicates that PTEN may function as a direct antagonist of PI-3 kinase and PIP-3 dependent signaling. Accordingly, PI-3 kinase inhibitors, such as LY294002, should be efficacious in blocking matrix degradation, invasion and metastasis of tumors in vivo. Finally, since these pathways are also important in wound healing, the data provide the first mechanistic link between PI-3 kinase signaling pathways and PTEN signaling pathways in the control of wound healing and wound associated angiogenesis.

EXAMPLE III

Inflammatory Signaling Downstream of Fc Receptor Activation is Modulated by Agents that Alter Tyrosine Kinase and Phosphatase Activity Fc gamma receptor mediated phagocytosis is a model for immunoreceptor (ITAM) signaling and involves the activation of protein tyrosine kinases and protein tyrosine phosphatases. Relatively little is known of role of lipid phosphatases in control of ITAM signaling and inflammation. We used phagocytic J774A.1 cells and a heterologous COS7 cell system to examine the roles played by Src family of protein tyrosine kinases, Syk and PI-3 kinase and protein tyrosine phosphatase, PTEN in signal transduction pathway leading to Fcγ receptor mediated phagocytosis. Heterologous expression of dominant negative Syk in J774A.1 cells significantly inhibited phagocytosis of sensitized sRBCs and preincubation of the cells with the Src specific protein tyrosine kinase inhibitor, PP1, and PI-3 kinase inhibitor, Wortmannin, was shown to inhibit this response. Stimulation of J774A.1 cells with sensitized sRBCs induced tyrosine phosphorylation of Cbl, which was inhibited significantly by PP1 and to some extent by heterologous expression of dominant negative Syk implicating Src and syk in the phosphorylation of Cbl in phagocytic signal transduction. The heterologous overexpression of PTEN completely abrogated the phagocytosis of IgG sensitized sheep red blood cells (sRBCs) compared to catalytically inactive mutant of PTEN. These data provide the first evidence that PTEN, a tyrosine phosphatase, is involved in the regulation of Fcγ receptor mediated phagocytosis and the regulation of immunoreceptor tyrosine based activation motif (ITAM) based signaling events in hematopoietic cells.

Overexpression of a catalytically dead PTEN phosphatase resulted in augmented phosphorylation of AKT and augmentation of phagocytosis and ITAM signaling. These results show that activating signals provided by Src family kinases, Syk and PI-3 kinase are opposed by inhibitory signals through PTEN in the control of Fcγ receptor mediated phagocytosis. Thus, PTEN agonists and PI-3 kinase inhibitors should provide potent anti-inflammatory and immunosuppressive agents to control downstream signaling events mediated by ITAM linked receptors found in hematopoeitic cells (e.g., T cell receptor, B cell receptor, Fc receptors and collagen receptor VI). Such agents should also exert potent control over the immune responses mediated through T cells, B cells, myeloid cells including macrophages, neutrophils, dendritic cells, monocytes, mast cells and platelets by preventing their activation and subsequent modulation of unwanted immune reactivity and platelet aggregation which contribute to a number of human diseases.

The following methods and materials are provided to facilitate the practice of Example III.

Anti-Cbl antibody was obtained from Santa Cruz Biotechnology, Santa Cruz, Calif. Anti-Syk antibody was provided by Dr. Tamara Hurley (The Salk Institute, San Diego, Calif.) and anti-PTEN antibody was generated by immunizing rabbits with an N-terminal peptide of PTEN.

J774A.1, a macrophage-like cell line, and Cos 7 cells were obtained from the ATCC. Both cell lines were maintained in DMEM supplemented with 10% fetal calf serum (FCS). Recombinant vaccinia virus vectors were provided by Dr. Bernard Moss (National Institutes of Health, Bethesda, Md.). The dominant negative Syk vaccinia construct (encoding the amino terminal residues 1–255 of Syk) which also encodes beta-galactosidase was provided by Dr A. Scharenberg (Sharenberg et al., (1995) Embo J. 14:3385). Recombinant vaccinia viruses containing PTEN and dominant negative Syk were prepared as described below.

Briefly, recombinant vaccinia viruses were propagated in 149B cells grown in RPMI medium containing 10% FCS. A confluent culture of cells was infected with recombinant vaccinia virus at a concentration of 0.5 pfu/cell for 48 h. The cells were scraped from the plastic in the same medium, centrifuged to generate a cell pellet, and resuspended in 5 ml of 10 mM Tris-HCl (pH 9). The cells were lysed by three cycles of freezing in liquid nitrogen and thawing at 37° C., after which the volume of the cell lysate was adjusted to 20 ml with 10 mM Tris-HCl (pH 9) in preparation for mechanical lysis step provided by forty strokes in a homogenizer. Nuclei and cell debris were separated from the cell lysate by centrifugation at 1,000 rpm for 5 min. The cell lysate containing the recombinant vaccinia virus was then subjected to sonication for 1 min with 50% output and a 30% duty cycle. The cell lysate was loaded on a cushion of 36% sucrose solution and centrifuged at 13,000 rpm for 80 min 4° C. in an ultracentrifuge (Beckman, Palo Alto, Calif.) using a SW.28 rotor. Viral pellets obtained were resuspended in 1 ml of 10 mM Tris-HCl (pH 9) and loaded onto a sucrose gradient composed of 6.6 ml each of 40%, 36%, 32%, 28% and 24% of sucrose solutions made in 10 mM Tris-HCl (pH 9) to be centrifuged at 12,500 rpm for 50 min at 4° C. in an ultracentrifuge using a SW.28 rotor. A bluish white ring containing purified virus was collected and diluted with 10 mM Tris-HCl (pH 9) prior to a final centrifugation at 13,000 rpm for 60 min at 4° C. in an ultracentrifuge using a SW.28 rotor to pellet the virus. Purified recombinant vaccinia virus thus obtained was suspended in 10 mM Tris-HCl (pH 9) and titered as followed. An aliquot was used for generating serial dilutions of the concentrated viral suspension. The serial dilutions were used to infect a confluent lawn of 149B cells grown in 35 mm wells for 2 h at 37° C. in 1 ml of RPMI medium containing 10% FCS. The medium was then replaced with 3 ml of fresh RPMI medium containing 10% FCS. The medium was discarded after 24 hours incubation and viral plaques were visualized by staining with crystal violet to titer the virus.

A DNA construct encoding the catalytically dead trap mutant of PTEN, C124S, was kindly provided by Nicholas Tonks (Cold Spring Harbor Laboratory, Cold Spring Harbor, N.Y.). This mutant The PTEN insert was amplified by PCR using the following 5' and 3' primers:

```
5'GG-GTC-CAC-ATG-ACA-GCC-ATC-ATC-AAA-GAG'3'      forward primer (SEQ ID NO: 19) and 5'-GG-TCT-AGA-TCA-GAC-TTT-TGT-AAT-TTG-TGA'3'     reverse primer (SEQ ID NO: 20),
``` respectively. The amplified product was subcloned into the PCR2.1 vector for propagation using the TA cloning kit (Invitrogen, San Diego, Calif.), and the PTEN insert was cleaved from the vector by digestion with SmaI and SalI and subsequently ligated into a linearized recombinant vaccinia vector pSC65 to generate pSC65-PTEN. The construct C2pSC65 was used to make a recombinant vaccinia virus using the packaging cell line CV1 and the wild type vaccinia virus. Recombinant virus was isolated from wild type virus by single plaque purification, and then amplified, purified, and titered as described above.

J774A.1 phagocytic cells were plated at $2 \times 10^5$ cells per well in a twelve well plate (Costar, Corning, NY) and cultured overnight. Cells were infected with recombinant vaccinia virus pSC65 or pSC65-PTEN at a density of 2 pfu/cell for 4 h at 37° C. in 5% $CO_2$. The media was changed after 4 hours and the cells were incubated with sheep red blood cells coated with IgG at a subagglutinating concentration. The target to effector ratio was 100:1. The cells were harvested after 2 hours, and cytospins were prepared, fixed, and stained with Wright Giemsa stain (Dade, AG, Switzerland). Stained slides were evaluated microscopically for rosette formation. The remaining uningested sRBCs were subjected to lysis by osmotic shock in water. The cells were suspended in DMEM medium containing 20% FCS. The cells were spun down on glass slide and fixed and stained by Wright Giemsa stain. A minimum of one hundred and fifty cells were counted for each slide and the phagocytic index was calculated as follows: Phagocytic Index (PI)=% of phagocytic cells x average number of sRBCs engulfed by each cell.

In the drug inhibition studies, the cells were subjected to treatment with an indicated inhibitor at different concentrations along with an appropriate DMSO control for 1 hour in DMEM with 10% FCS before carrying out the phagocytic assay.

Assays to detect β-galactosidase activity were performed as follows: cells (1×10⁵) were suspended in 400 μl of DMEM containing 10% FCS to which 50 μl of 1% X-gal (Sigma, St.Louis, Mo.) was added. Subsequent incubation at 37° C. facilitates β-galactosidase activity which is indicated by acquisition of a blue color by the reaction mixture. The reaction mixture was diluted 1:10 and the optical density was measured at 595 nm in a spectrophotometer (Molecular Devices, Menlo Park, Calif.).

J774A.1 cells and COS7 cells (2×10⁵) infected with recombinant viruses expressing either dominant negative Syk or PTEN were lysed in 50 μl of sample buffer. The lysates were resolved by SDS-PAGE, transferred to a solid matrix support, and probed to assess protein expression with specific antibodies.

J774A.1 cells were infected with recombinant vaccinia virus at the concentration of 2 pfu/ml for 4 hours. The infected cells were then pelleted by centrifugation, and resuspended at a concentration of 2×10⁶ cells per ml in DMEM to be stimulated with IgG coated sRBCs at 37° C. for 5 min. The samples were pelleted at 500× g in a refrigerated centrifuge and the resultant cell pellet was lysed as described earlier and analyzed following immunoprecipitation with specific antibodies.

Dominant Negative Syk Inhibits Phagocytosis

Figure 9A:
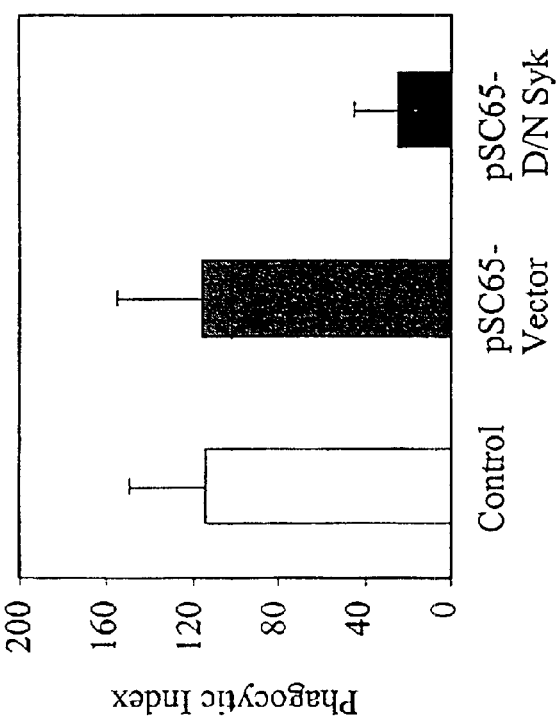
FIGS. 9A and 9B are a graph and a blot showing that dominant negative Syk inhibits phagocytosis The phagocytosis of IgG sensitized sRBCs by J774A.1 was measured in cells infected with empty vector recombinant vaccinia virus or virus containing dominant negative Syk (D/N Syk). The cells were infected with the respective viruses for 4 h at 37° C. with 5% $CO_2$, after which they were subjected to IgG sensitized sRBCs in fresh medium at a target to effector ratio equal to 100:1 for 2 h at 37° C. with 5% $CO_2$. Nonengulfed sRBCs were lysed by water shock and the cells were fixed and stained with Wright-Giemsa staining before counting the phagocytic index.
Figure 9B:
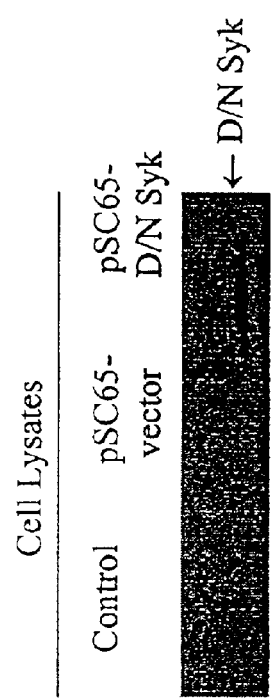

In order to investigate the role played by the nonreceptor tyrosine kinase Syk in IgG mediated phagocytosis, a dominant negative mutant form of Syk was expressed in J774A.1 cells utilizing recombinant vaccinia virus as a means of transmission. This Syk mutant encodes a truncated form of Syk which comprises the tandem SH2 domains, but excludes the catalytic domain. As a result of this mutation, the protein behaves as a dominant negative mutant by binding to the ITAMs of the FcγR subunit, thereby blocking the interaction of the endogenous catalytically active Syk with these sites. The results demonstrated that the expression of dominant negative Syk in J774A.1 cells inhibited phagocytosis of IgG coated sRBCs (FIG. 9A). In contrast, J774A.1 cells infected with empty vector recombinant vaccinia virus, as a control, engulfed sensitized sRBCs normally. The expression levels of dominant negative Syk in infected cells was evaluated by Western analysis using antibodies specific for Syk (FIG. 9B, lane 3). To ensure that the inhibitory effect on phagocytosis was specific to the expression of dominant negative Syk, and not a consequence of differential levels of viral infection, infected J774A.1 cells were assessed for viral load. Since the pSC65 plasmid, into which the dominant negative Syk was cloned, also contained the gene encoding β-galactosidase, this enzyme was used as an internal control for viral expression levels. Briefly, β-galactosidase activity can be quantified calorimetrically as indicated by the appearance of a colored product following cleavage of the substrate X-gal. In every experiment, the levels of recombinant viral load were equivalent to those of control cells (infected with empty vector recombinant vaccinia virus) and experimental cells (infected with vaccinia virus containing dominant negative Syk; data not shown).

As an additional control to evaluate the specificity of the inhibition observed after expression of dominant negative Syk, the capacity of J774A.1 cells to form rosettes via the FcγR was examined following infection with different viruses. Cells infected with empty vector recombinant vaccinia virus and cells infected with vaccinia virus containing dominant negative Syk displayed 100% rosette formation within 1 minute of addition of sensitized sRBCs; these data indicated that neither the cell surface expression level of FcγRs nor their binding capacity for sRBC targets was affected by infection with recombinant vaccinia virus alone (data not shown). Notably, rosette formation and phagocytosis did not occur in the absence of sensitizing antibody against sRBCs, thereby further underscoring the specificity of these responses. These data using dominant negative Syk were consistent with other data in the literature, including those derived from Syk knockout mice (Crowley, M., et al., (1997) J. Exp. Med. 186:1027), which strongly support a role for Syk in propagating signals required for IgG mediated phagocytosis in the J774 system.

Figure 10A:
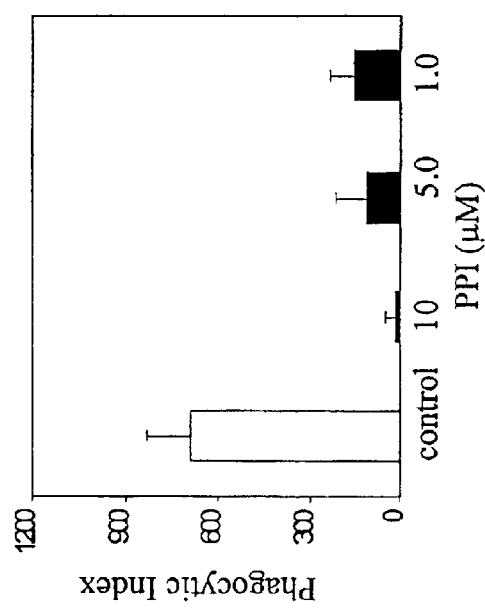
FIGS. 10A and 10B are graphs showing that Src and PI-3 kinase are required for ITAM signaling. Cells were treated with PP1, an inhibitor of Src family kinases, at concentrations of 10, 5 and 1 $\mu$M or wortmannin, an inhibitor of PI-3 kinase, at concentrations of 10, 5 and 1 $\mu$g/ml along with an appropriate DMSO control for 1 h in DMEM with 10% FCS and then sensitized sRBCs were added at target to effector ratio equal to 100:1.
Figure 10B:
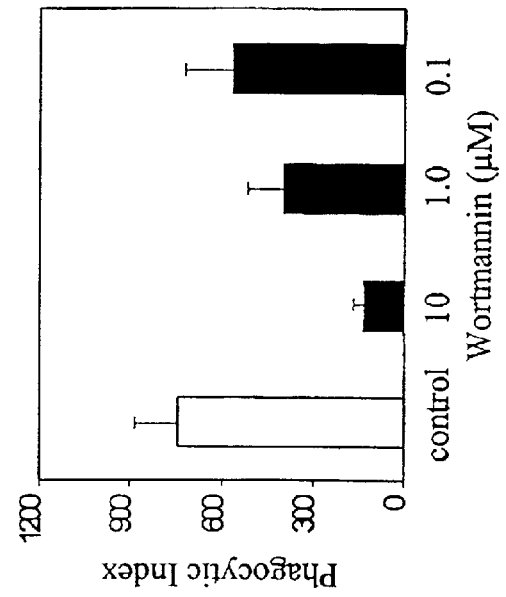

Src and PI-3 Kinase are Required for Phagocytosis of IgG Coated sRBCs by J774A.1 Cells Recent evidence from Hck,/Lyn/Fgr knockout mice suggests that members of the Src family of nonreceptor protein tyrosine kinases function upstream of Syk and PI-3 kinase in ITAM signaling (Crowley et al., 1997, supra). To examine the role of Src in FcγR-mediated phagocytosis, J774 cells were treated with different concentrations of PP1 (1, 5, or 10 μM; Calbiochem, La Jolla, Calif.), a Src family tyrosine kinase inhibitor, wortmannin(1 or 5 μg/ml), an inhibitor of PI-3 kinase (LY294002), or DMSO as a control. Briefly cells were treated with the above reagents for 1 hour in DMEM supplemented with 10% FCS and then sensitized sRBCs were added at a target to effector ratio of 100:1. As shown by FIG. 10A, PP1 inhibited phagocytosis in a dose dependent manner and completely abrogated phagocytosis at a 10 μM concentration. As shown in FIG. 10B, 5 μg/ml wortmannin also mediated significant inhibition of phagocytosis. These observations implicate the Src kinase family and PI-3 kinase in IgG-mediated phagocytosis of sRBCs by J774A.1 cells.

Figure 11A:
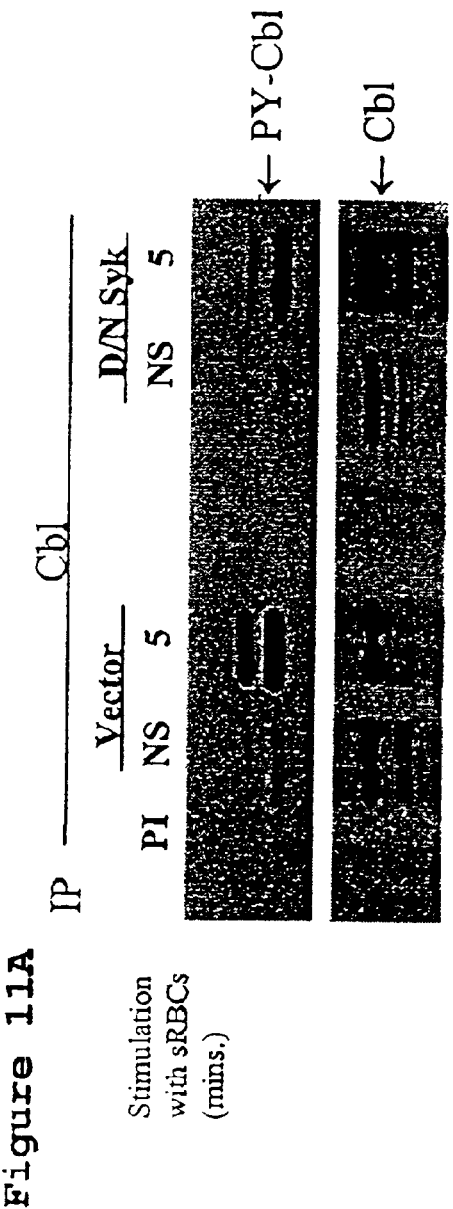
FIGS. 11A and 11B are blots showing the effect of a dominant negative Syk and Src inhibitor, PP1, on tyrosine phosphorylation of Cbl in response to ITAM stimulation.
Figure 11B:
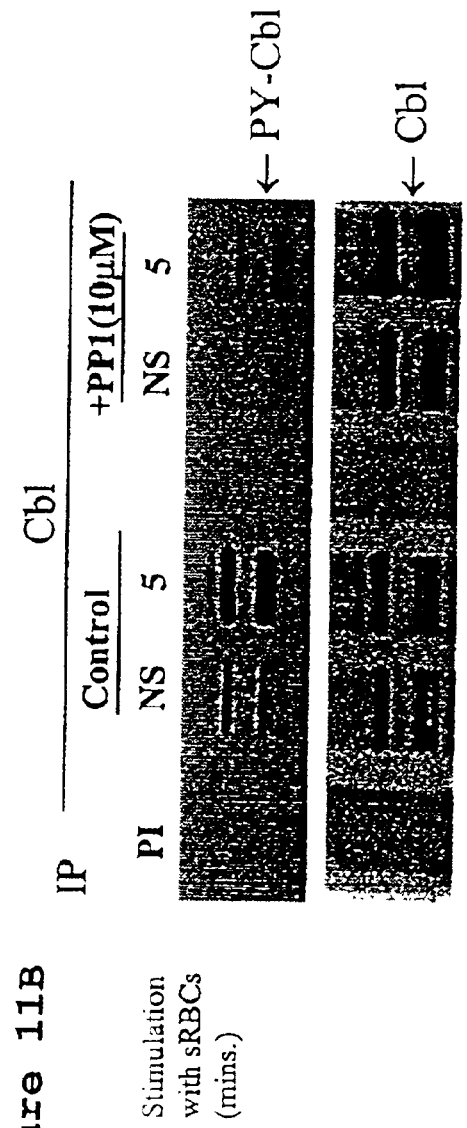

Effect of Dominant Negative Syk and Src Inhibitor, PP1, on Tyrosine Phosphorylation of Cbl in Response to Stimulation with Sensitized sRBCs It is well known that Fcγ receptor crosslinking induces the tyrosine phosphorylation of the adapter protein, Cbl (Park, R. K., et al., (1996) J. Immumology 160:5018). To determine if phagocytic signaling events lead to the phosphorylation of Cbl, the degree of Cbl phosphorylation was assessed before and after induction of phagocytosis. To investigate the role of specific kinases in this phosphorylation event, dominant negative Syk and the Src family kinase inhibitor PP1 were utilized to inhibit the activity of these enzymes. The results demonstrated that Cbl was phosphorylated on tyrosine residues following induction of phagocytosis and this phosphorylation event was abrogated by PP1 (FIGS. 11A and 11B, compare lanes 2–3 to 5–6). This effect was dose dependent (data not shown), as was the effect of PP1 on inhibition of Fcγ receptor-mediated phagocytosis (FIG. 11A). Interestingly, dominant negative Syk inhibited Cbl tyrosine phosphorylation to a lesser extent but completely abrogated the phagocytic response. Interestingly, both PP1 and dominant negative Syk suppressed the basal tyrosine phosphorylation levels of Cbl in vivo. These data suggested that the catalytic activity of the Src family kinases and the capacity of Syk to dock with the ITAM receptor were both required for Cbl phosphorylation in response to phagocytic stimuli and that these two events were required for phagocytosis. The dominant negative Syk would not be expected to alter the upstream activity of Src family kinases and hence Src mediated phosphorylation of Cbl was not altered to the same extent. The data provided support for a signaling cascade in which Syk functions downstream of Src and upstream of Cbl and other effectors associated with Cbl such as the p85 subunit of PI-3 kinase. The data demonstrated that Src family kinases mediated the phosphorylation of Cbl in a Syk kinase independent manner in vivo. The data also revealed that Src family kinases and Syk were required for phagocytosis mediated by the downstream activation of PI-3 kinase.

Of note, more recent data identified the tyrosine residue at position 731 of Cbl as a consensus binding site (YxxM; SEQ ID NO: 21) for the p85 regulatory subunit of PI-3 kinase. Upon phosphorylation, this motif was recognized as a target for PTEN (data not shown). Hence, PTEN plays a signaling role in regulation of ITAMs action on PI-3 kinase to control ITAM signaling events.

Overexpression of PTEN in COS7 System Inhibits FcγRIIA ITAM Signaling

Figure 12:
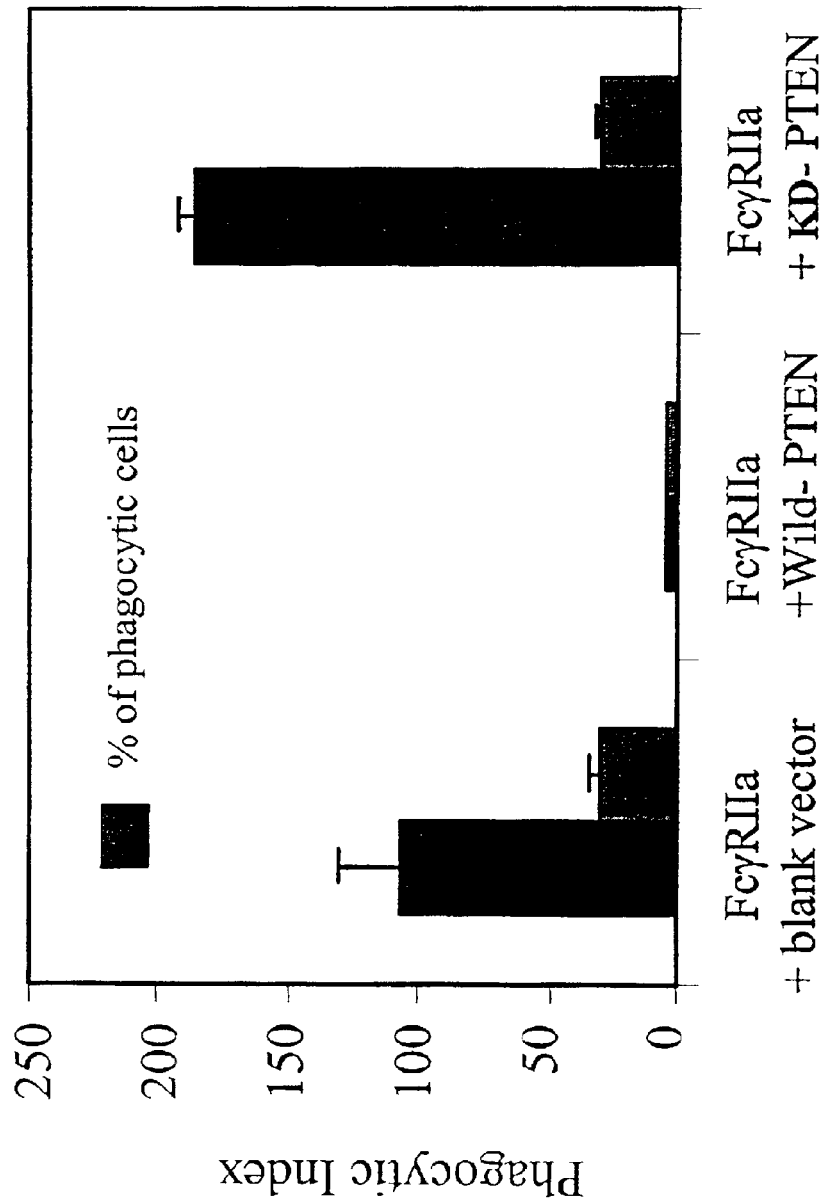
FIG. 12 is a graph showing that overexpression of PTEN in COS7 cells inhibits ITAM signaling. Shows phagocytosis of IgG sensitized sRBCs by COS cells transfected with Fc$\gamma$RIIa receptor, Syk, Cbl, PTEN or a trap mutant (C124S) of PTEN. The cells were transfected with episomal plasmids containing Syk, Cbl and/or PTEN for 12 h at 37° C. with 5% $CO_2$, after which were subjected to IgG sensitized sRBCs in fresh medium at a target to effector ratio equal to 100:1 for two h at 37° C. with 5% $CO_2$. All experimental groups were transfected with FcR$\gamma$IIA, Syk, and Cbl, data for Syk and Cbl, not shown. Nonengulfed sRBCs were lysed by water shock and the cells were fixed and stained with Wright-Giemsa staining before counting the phagocytic index. A graphic representation of the inhibition of phagocytosis of IgG coated sRBCs by COS7 cells overexpressing PTEN is shown. The error bars represent standard deviation of the mean. The red columns indicate the phagocytic index of plain J774A.1 cells transfected with plasmid containing vector only or PTEN. The green bars represent effect of PTEN on the percent of cells phagocytic for at least one SRBC.

Since tyrosine kinases are required for phagocytosis and lead to the activation of PI-3 kinase which phosphorylates phospholipids that act as second messengers, dephosphorylation of such phosphoinositides may serve a role to down-regulate this response. To address this issue, J774A.1 and COS7 cells were genetically engineered to overexpress the dual specificity phosphatase PTEN, which is known to dephosphorylate PIP3, a critical phosphoinositide second messenger. Overexpression of PTEN in COS7 cells markedly inhibited phagocytosis of IgG coated sRBCs (FIG. 12). PTEN expression reduced the phagocytic index (FIG. 12) by 95% as compared to that of control cells. In contrast, the C124S mutant of PTEN, which is catalytically dead and can act as a substrate trap, augmented the phagocytic index by a factor of 2.5. See FIG. 12. The green bars represent the percent of the total cell population which was phagocytic for at least one sRBC. These results demonstrated that PTEN negatively regulated IgG-mediated phagocytosis and that the catalytic activity of PTEN was required for this suppression.

These data provide further evidence for the role of PTEN in the regulation of ITAM-mediated signaling in a variety of signal transduction cascades essential for the propagation of the inflammatory response in T cells, B cells and myeloid cells. Accordingly, such biological processes provide the basis for methods for screening and identifying therapeutic agents which regulate these inflammatory responses.

Our observations suggest that the protein tyrosine kinases, Hck and Syk and PI-3 kinase are activated during FcγR mediated phagocytosis. Stimulation of macrophage cells with IgG coated particles activates FcγRs, FcγRI and FcγRIII in turn activate Hck/Src kinase which phosphorylates tyrosine in the ITAM motif in gamma chain associated with these receptors. This provides a site for attachment and activation for Syk, which would activate the pathway downstream leading to subsequent activatation of PI3-kinase which is needed for proper cytoskeletal assembly. On the other hand aggregation of FcγRIIB stimulates phosphorylation of tyrosine in its ITIM motif to provide a site of attachment and activation for phosphatases like PTEN and SHIP which in turn regulate the pathway downstream.

Consistent with our data using wortmannin, the 5' inositide phosphatase, SHIP, serves as a negative regulator of AKT phosphorylation and controls FcγR phagocytosis. Maeda et.al have provided evidence for the existence of two opposite signaling pathways upon aggregation of paired immunoglobulin receptors PIR-A and PIR-B (Maeda et al. (1998) J. of Exp. Med. 188:991) PIR-A induces the stimulatory signal by using ITAM in the associated γ chain while PIR-B mediates the inhibitory signal through its ITIM. Our results are consistent with the model that during Fcγ receptor mediated phagocytosis in J774A.1 mouse macrophages the FcγRI and FcγRIII utilize the ITAM motif to send a positive signal inside the cell for phagocytic pathway; whereas FcγRIIB controls the pathway by starting a negative regulatory loop via the ITIM motif through PTEN. Accordingly, Syk and Src inhibitors should suppress ITAM immunoreceptor signaling and control inflammation in concert with PI-3 kinase antagonists. It is also likely that synergy will exist when agents which inhibit more than one ITAM pathway are combined in humans.

In summary, the data support the involvement of Syk, Src family kinases and phosphatidyl inositol 3-kinase in positive regulation of Fcγ receptors mediated phagocytosis in our system. Described herein is the first evidence for the involvement of the protein/lipid phosphatase, PTEN in the negative regulation of phagocytosis and ITAM signaling. These data provide the basis for screening and identification of therapeutic agents that modulate PTEN, PI-3 kinase or the signaling pathways downstream of PI-3 kinase (PDK-1, PAK, AKT, forkhead, etc). Inhibitors of ITAM propagated signals (e.g., 1) T cell receptor/CD3 complex signaling in T cells; 2) B cell receptor signaling in B cells; 3) ITAM receptor signaling including Fcγ receptors which mediate myeloid inflammatory diseases through the production of inflammatory cytokines, TNFa, IL-1, IL-4 etc.; 4) the FCεRI receptor in mast cells responsible for atopic disease and allergy; and 5) the FcαRI involved in mucosal allergic responses) should effectively regulate the immune response pathway. Hence PTEN agonists and PI-3 kinase inhibitors should effectively modulate immunopathologic states in animals. Likewise Syk and Src kinase inhibitors should effect ITAM myeloid signaling.

EXAMPLE IV

PTEN and PI-3 Kinase Signaling Cascade Regulates p53 and Tumor-Induced Angiogenesis As described in Examples I, II and III, PTEN regulates the tumor-induced angiogenic response and thrombospondin expression in a malignant glioma model. A recent report by Sabbatini et al suggests a connection between the PI-3 kinase cascade and the regulation of p53 signaling (Sabbatini, 1999; J. Biol. Chem. 274:24263). Activation of PI-3 kinase/AKT pathways results in the suppression of p53 dependent apoptotic pathways giving rise to conditions that are permissive for cell division. These data suggest a molecular mechanism for the coordination of signals coming from growth factor receptors through PI-3 kinase cascades which would jointly regulate apoptosis, proliferation and recruitment of a new blood supply (neovascularization/angiogenesis). This signaling pathway appears to be tightly regulated in normal tissues. During malignant transformation, this coordinated regulation of cellular signaling is lost. In the present example, we demonstrate that PTEN plays a role in coordinating these signaling events within the cell. We also show that loss of PTEN leads to deregulation and tumor progression. Bearing in mind the link between PTEN phosphatase activity and PI-3 kinase signaling pathways, we performed assays to determine whether PI-3 kinase inhibitors were capable of reestablishing this regulatory feedback system thereby restoring normal coordination of cell growth and angiogenesis.

Thrombospondin 1 (TSP-1), angiostatin, endostatin, tissue inhibitors of metalloproteinases (TIMPs) are potent inhibitors of angiogenesis (Dameron, et al.,(1994) Science 265:1582; Good et al., (1990)PNAS 87:6624). Malignant brain tumors are known to undergo a more robust angiogenic response as compared to their benign low-grade counterparts, and are classified histopathologically by the presence or absence of high microvessel counts (microvessel density)(MVD). Regulation of PI-3 kinase-dependent signals, including activation of AKT by Vascular Endothelial cell Growth Factor and its receptors, the protein tyrosine kinases Flt-1 and KDR, have been implicated in brain tumor angiogenesis (Plate et al.,(1992) Nature 359:845). Jiang et al demonstrated in the chicken chorioallantoic membrane model that PI-3 kinase-dependent pathways may regulate angiogenesis and VEGF expression in endothelial cells (Jiang et al., (2000) PNAS 97:1749). Immunohistochemical studies in prostate tumor specimens have demonstrated that tumors containing PTEN mutations have higher microvessel counts than tumors expressing wild type PTEN (Giri et al., (1999) Hum. Pathol. 30:419).

To test the hypothesis that PTEN is connected to p53 transcription we performed experiments in U87MG glioma cell lines which are wild type for p53 and deficient in PTEN. We conditionally expressed in these U87MG cells, wild type PTEN or catalytically defective mutants of PTEN to determine if PTEN regulates p53 transcription. We then performed experiments with the PI-3 kinase inhibitor using the parental U87MG cells to determine if LY294002 control over $PIP_3$ metabolism would prevent tumor growth and block angiogenesis in vivo.

The following protocols are provided to facilitate the practice of Example IV.

The constructs and encoding the PTEN mutants have been previously described in Example I. Tumor implantation methods are also provided in the previous examples.

Treatment of Mice with LY294002.

LY294002 was administered at a dosage of 100 mg/kg delivered daily by intraperitoneal injection in a small volume of 100% DMSO for 2 weeks, beginning 2 days after tumor implantation. No untoward effects were noted in mice treated with either LY294002 or DMSO. Control mice were injected with small volume (10 ml) of 100% DMSO. Daily measurement of tumor volume was performed in 3 coordinates using calipers.

Biochemical Analysis.

Immunoblots were performed on cell lysates obtained from U87 cells grown in tissue culture or from multiple cryostat sections of subcutaneous tumor tissues. A Bradford assay was performed to determine protein concentration of each lysate. Equivalent amounts of protein were resolved by SDS PAGE and transferred to nitrocellulose. Membranes were probed with antisera specific for PTEN, AKT, phospho-S473-AKT. We used a well characterized mdm2 promoter linked to firefly luciferase (mdm2luc inserted into the pGL2 vector) that contains p53 DNA binding elements (Ouchi et al., (1998) PNAS 95:2302) to study p53 specific transcription in U87 cells under muristirone induced PTEN expression conditions. Another construct, pGL2, contained the mdm2luc promoter which is deleted for p53 response element was used as a negative control. Cells were cotransfected with pRSVβgal to normalize mdm2 luciferase activity for transfection efficiency. The Tropix-galacto-light kit and Promega luciferase assay system was used to quantitate β-galactosidase and luciferase activity, respectively.

Immunohistochemical and Histopathology.

Microvessel density (MVD) was determined for as described in the previous examples.

Results

Figure 13:
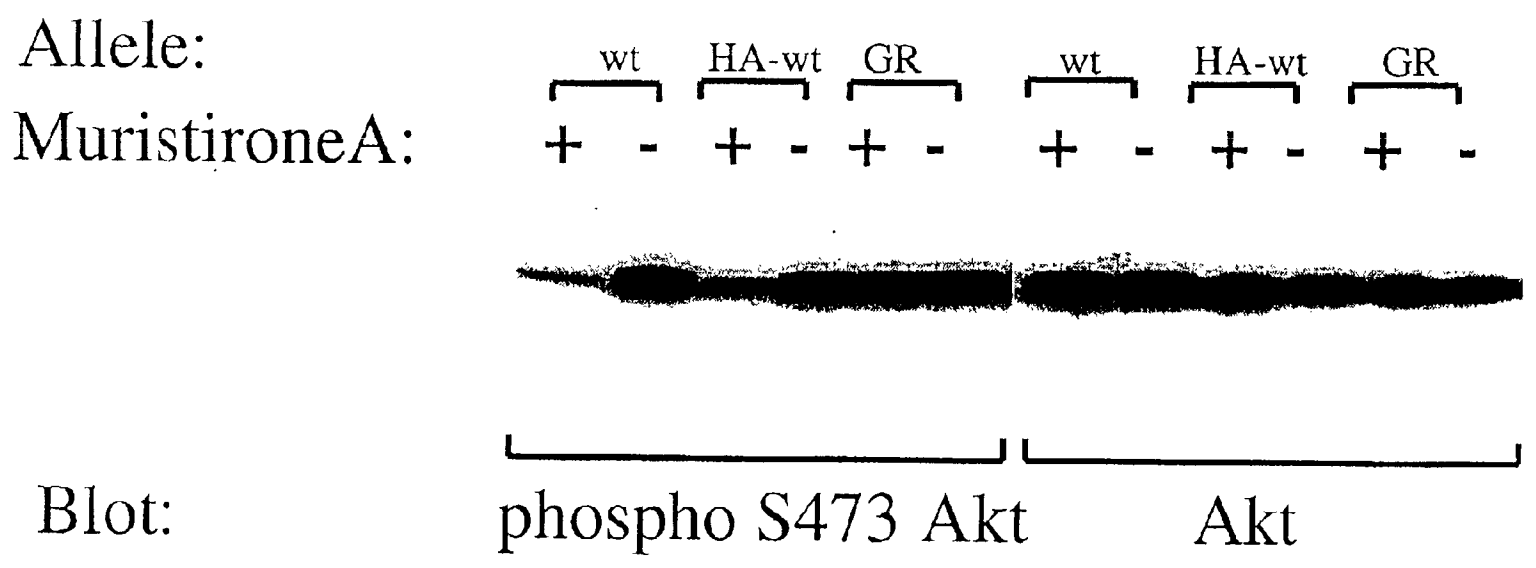

The previous examples demonstrated that the muristirone inducible expression of PTEN in U87 cells results in increased levels of thrombospondin 1 expression, a negative regulator of angiogenesis. In the present example, we demonstrate that wild type PTEN suppressed the activation of phospho-AKT without affecting total AKT (FIG. 13). The induced expression of mutant G129R had no effect on phosphoAKT (FIG. 13). The data presented in the previous examples indicate that PTEN may regulate angiogenesis through the induction of TSP-1. One transcription factor that upregulates TSP-1 is the tumor suppressor protein p53 (Dameron, (1994) Science 265:1582). We sought to determine if there was a link between PTEN, TSP1 and p53.

Figure 14:
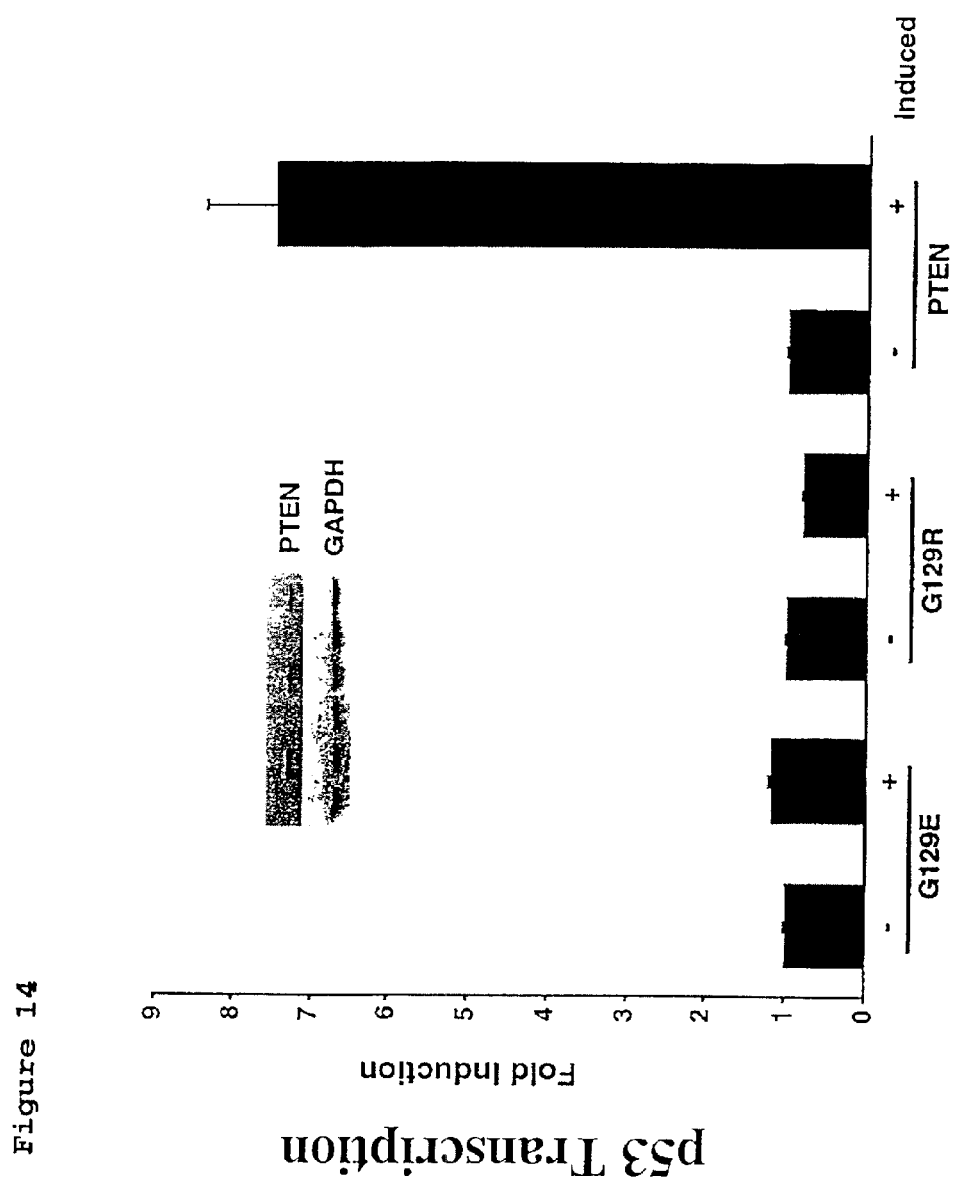
FIG. 14 is a graph and a blot showing the effect of PTEN induction on p53 transcription. U87MG cells expressing wild type PTEN, G129E or G129R mutants of PTEN under the control of muristirone (Western blot, insert) were transiently cotransfected with pRSV$\beta$-galactosidase and mdm2 luciferase. U87MG cells expressed similar levels of PTEN and G129R and slightly higher levels of G129E PTEN under control of a muristirone (+indicates muristirone added to cultures 24 hours prior to transfection of reporter plasmids; lanes correspond to columns of bar graph). Induction of p53 dependent transcription was quantitated using β galactosidase as an internal control for transfection efficiency.

The data presented herein demonstrate that PTEN regulates p53 transcription (FIG. 14). The induction of wild type PTEN and not mutant PTEN induced p53 dependent transcription in U87 cells (7.5-fold induction)(FIG. 14). Muristirone induced expression of wild type PTEN or G129R protein was equivalent whereas G129E induction was slightly greater (see insert, FIG. 14). Controls were performed using an mdm2luciferase construct deleted in critical p53 binding sites to confirm the specificity for PTEN induction of p53 specific transcription. These data provide compelling evidence that PTEN and p53 are linked in a common pathway and therefore provide new biochemical targets for influencing PTEN regulation of expression of TSP-1 through the regulation of p53 transcription.

Figure 15:
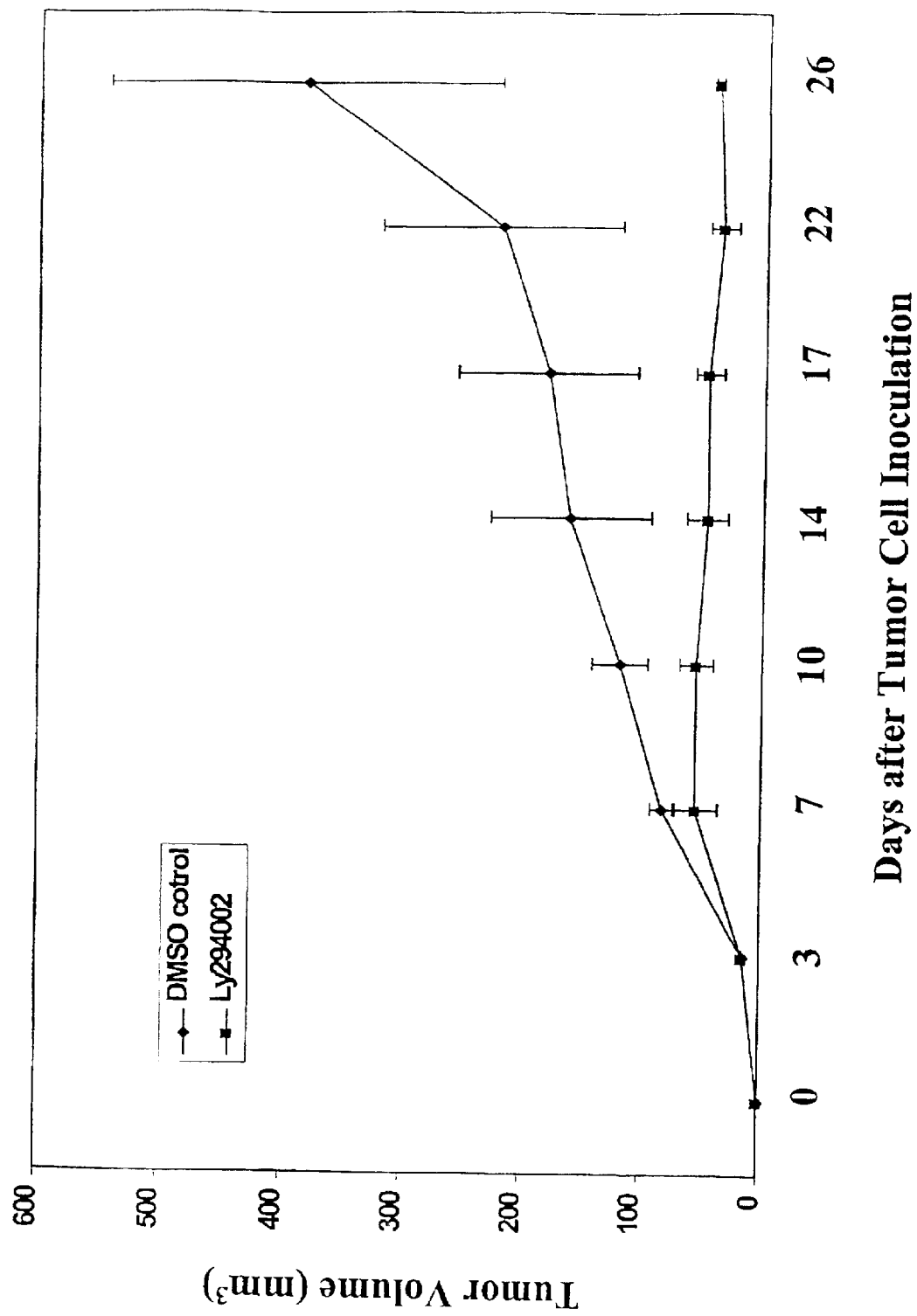
FIG. 15 is a graph showing that PI-3 kinase inhibitors block tumor growth. Tumor volume was measured in DMSO treated mice or LY294002 (a PI3 kinase inhibitor) treated (100 mg/kg/day×2 weeks) mice; treatment was concomitant with tumor implantation.
Figure 16:
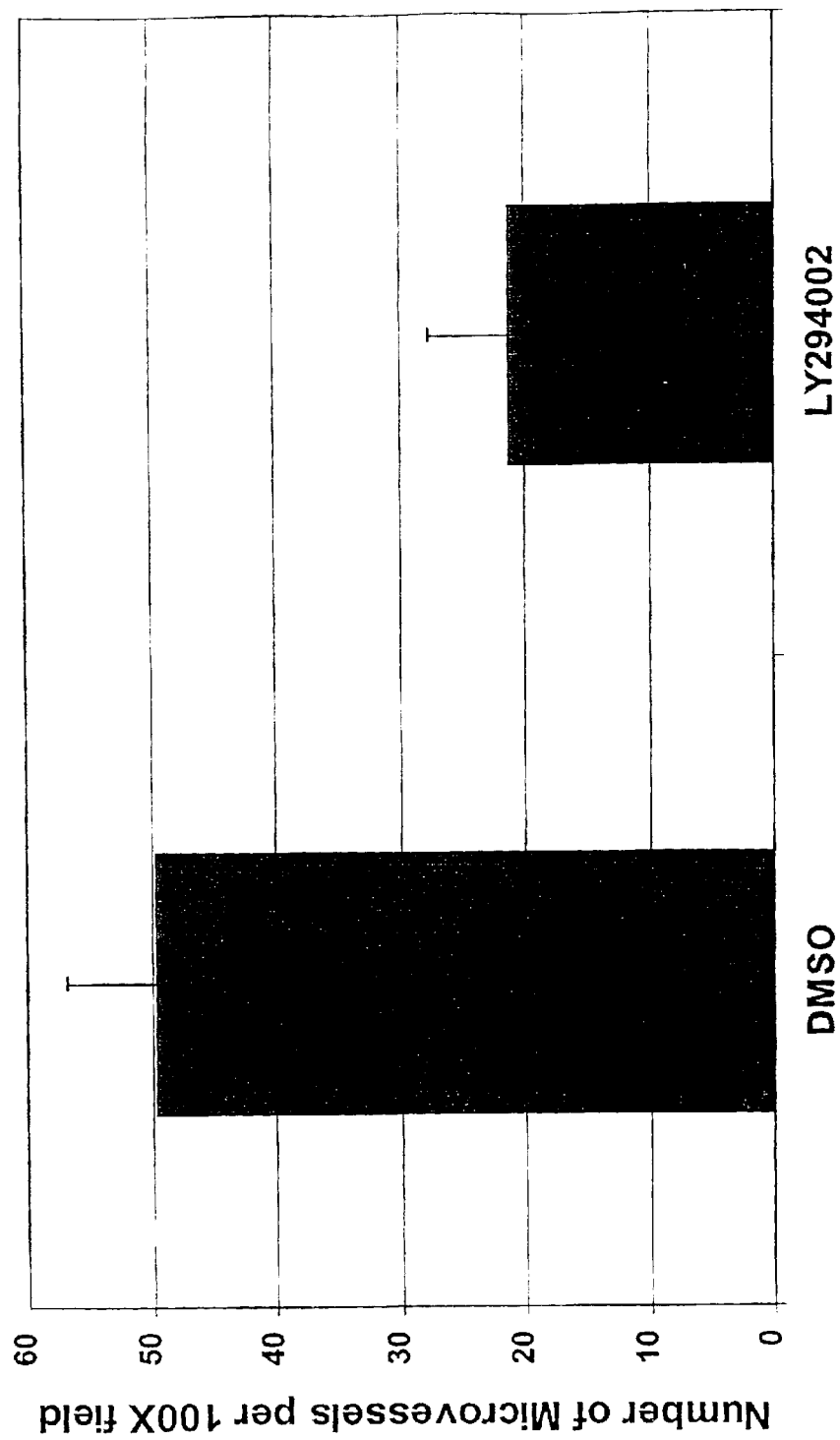
FIG. 16 is a graph showing quantitation of CD31 positive microvessels within tumor tissue in the presence and absence of LY294002. Note the dramatic inhibitory effect of LY294002 on tumor-induced angiogenesis. Bars represent standard deviation of the mean (p<0.001).

To determine whether PI-3 kinase exerts control over angiogenesis or the growth of glial tumors in vivo the orthotopic brain tumor model described in Example I was utilized. To assess the effect of LY294002 on angiogenesis, we treated mice with LY294002 (100 mg/kg/dose×2 weeks) or DMSO as negative control. Tumor volumes were recorded daily (FIG. 15). On day 14 we stained cryostat sections from subcutaneous tumors for CD31 (PECAM). CD31 is an endothelial marker used to measure the microvessel density of these tumors. Microvessel density was assessed from multiple digitized images of CD31-stained tumor tissue at 100× magnification (3 fields were evaluated per tumor) and counted blindly for the number of CD31 positive microvessels per unit surface area as described (Weidner et al., (1991) N. Engl. J. Med. 324:1). Quantitation of microvessel density in tumors treated with DMSO versus LY294002 are shown in FIG. 16. Compared to controls (FIG. 16), it was observed that LY294002 markedly suppressed the tumor-induced angiogenic response in this model (MVD is 22±5 in LY294002 treated tumors versus 50±6 in the controls). Importantly, microvessel determinations were performed on day 7 after implantation to compare angiogenic activity of tumors of similar size. At the time of analysis the tumors were approximately 400 mm3 in the control and approximately 35 mm3 in the LY294002 treated mice. These data argue against an effect of tumor hypoxia or size on the induction of angiogenesis. It is likely that the effects of LY294002 are complex and that the size of tumor mass may contribute at later time points to the induction of angiogenesis. Despite this caveat, the data demonstrate that LY294002 dramatically suppressed the angiogenic response of U87MG cells in vivo.

Figure 17:
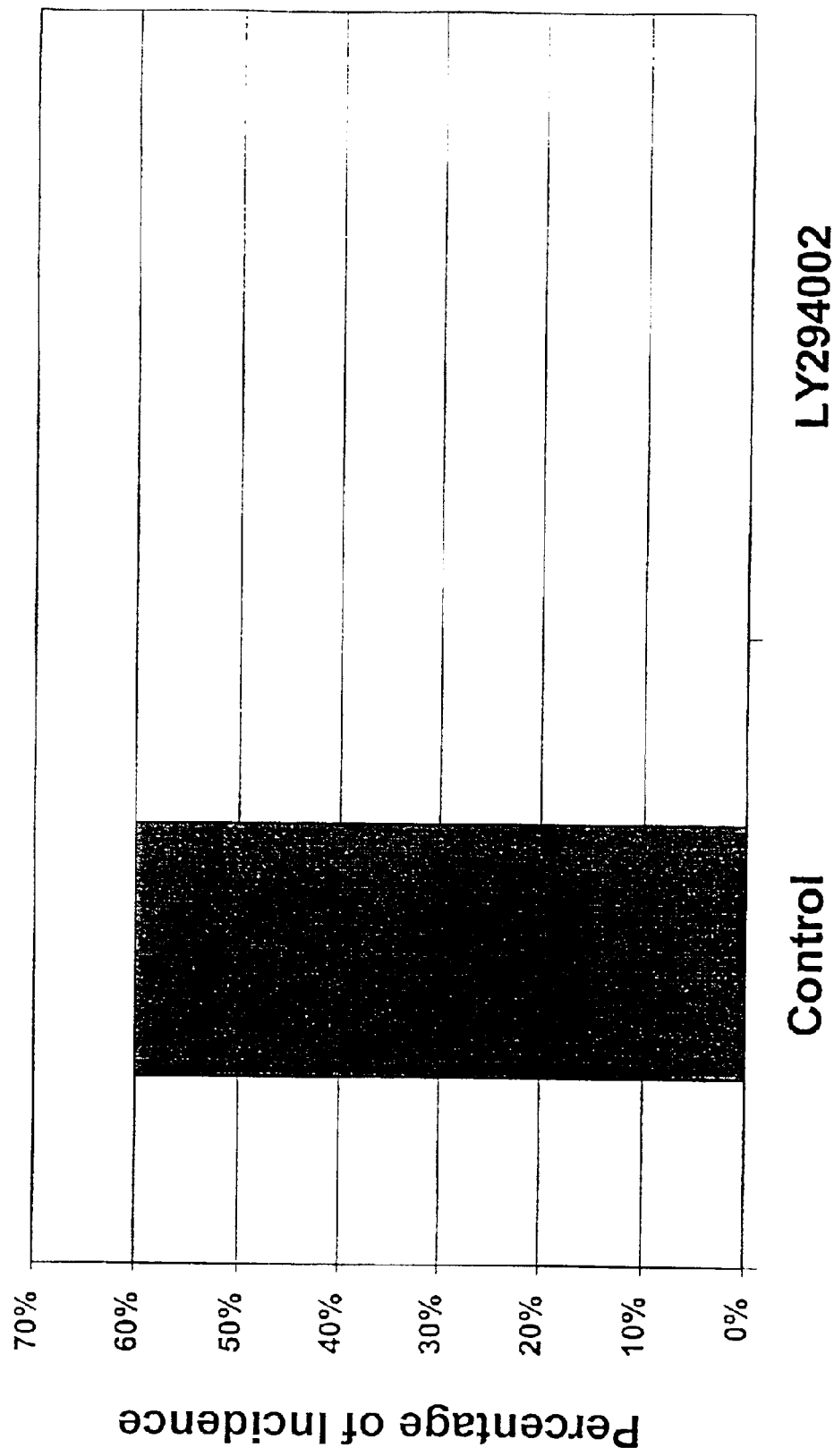
FIG. 17 is a graph showing that administration of LY294002 dramatically reduces the incidence of brain tumors.

We also examined the effect of LY294002 on tumor growth and incidence of brain tumor in a nude mouse model. See FIG. 17. In a previous study, in vivo activity of LY294002 against an ovarian carcinoma was observed. However, it is difficult to interpret these results as the tumor was grown as an ascitic tumor and LY294002 was injected into peritoneal cavity. In other words, the carcinoma was not assessed in its natural milieu. Hu et al., Clin. Can. Res. 6:880). Our results show conclusively that subcutaneous tumor growth is markedly suppressed by LY294002 treatment (FIGS. 15 and 17). In additional experiments, we observed that LY294002 markedly suppressed the intracranial growth of U87MG cells in nude mouse model. In control mice treated with DMSO, ⅘ had grossly visible and/or histologically confirmed brain tumors by H & E analysis by day 25 after implantation, whereas in ⅗ mice treated with LY294002 had grossly detectable or histologic evidence of intracranial tumor when examined on day 42. Other recent reports suggest that LY294002 and PTEN reconstitution may increase tumor responsiveness to DNA damage from chemotherapy and radiation. Our results suggest that PTEN exerts its regulatory effects through the induction of p53 transcription, a known factor in the induction of apoptosis.

Recent in vitro data suggest a link between PI-3 kinase and downstream targets including AKT, HIF1α and VEGF in the potential control of angiogenesis. In the present example, we show that the PTEN tumor suppressor controls p53 transcription in U87 glioblastoma cells. Holland et al recently reported that the introduction of activated AKT and Ras into glial cells of the mouse brain results in the development of glioblastomas (Holland et al., (2000) Nat. Genet. 25:55). Thus, the combined data indicate that inhibitors of PI-3 kinase and downstream targets such as AKT should provide therapeutic efficacy in the treatment of malignant gliomas. Finally, the results presented herein provide the first evidence that LY294002 controls tumor-induced angiogenesis through a mechanism that appears to involve the regulation of p53 transcription. Accordingly, these data support the hypothesis that these two tumor suppressor genes are localized on the same signaling pathway for the coordinated control of angiogenesis in tumor cells.

EXAMPLE V

PTEN Reconstitution Enhances Sensitivity of Tumors to Chemotherapy and Radiation Therapy in vitro and in vivo The data presented in Example IV demonstrate that a molecular link exists between the activities of PTEN and p53 tumor suppressor genes, p53-mediated transcription and phosphorylation of MDM2 by AKT. These data indicate that activation of the PI-3 kinase pathway can be correlated with a reduction of programmed cell death leading to a higher risk of tumor progression. Thus, agents which modulate the PTEN pathway can be used in certain cell populations to influence the apoptotic mechanisms triggered by chemotherapy and radiation and other cellular stresses. PI-3 kinase, MDM2 and AKT as well as PTEN provide ideal biological targets for the development of such agents. Thus, the present invention provides methods for identifying and biochemically characterizing small molecules which modulate the biological processes regulated by these proteins, including, but not limited to apoptosis, proliferation, differentiation and chemosensitivity.

Figure 18:
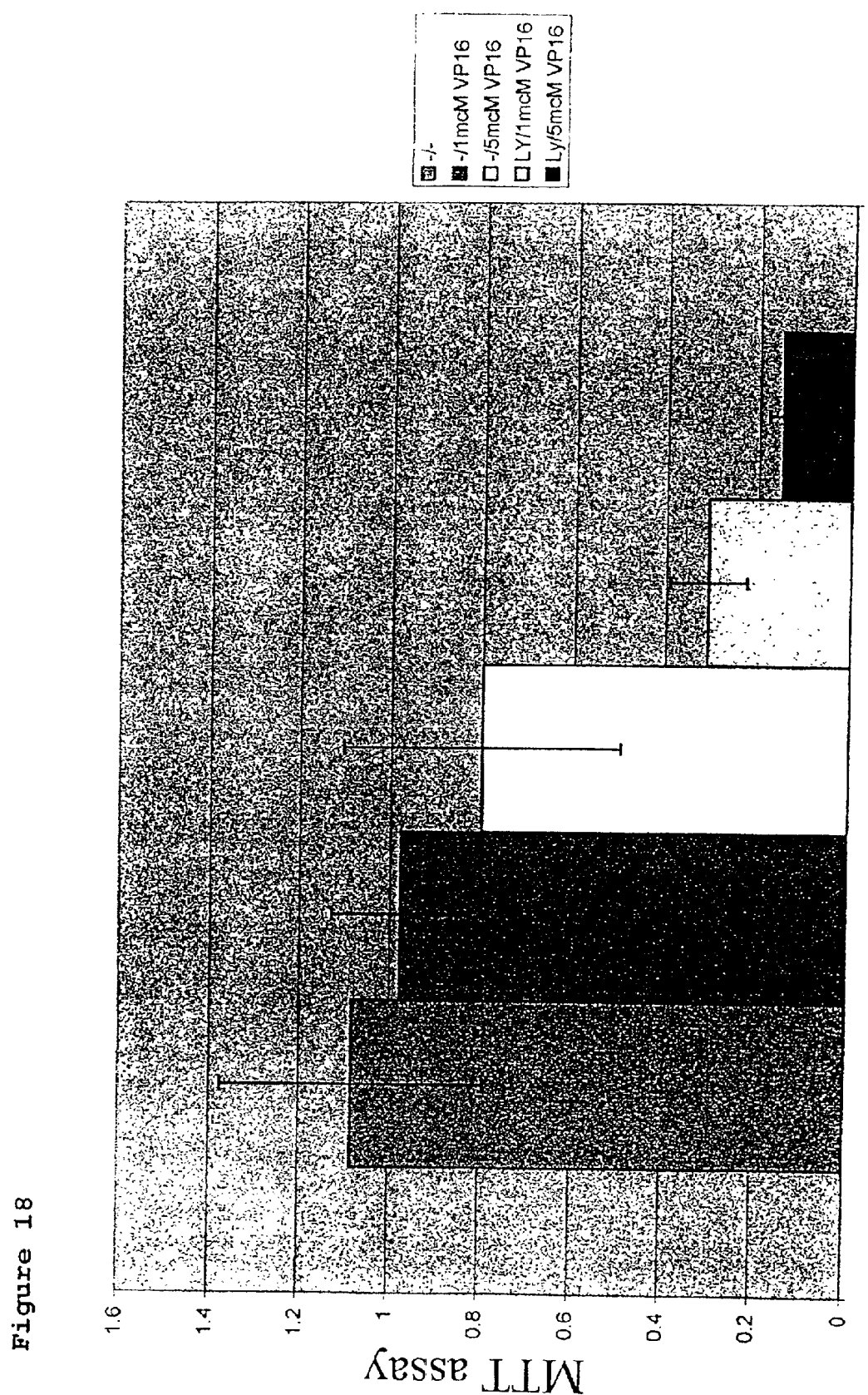
FIG. 18 is a graph showing that the effect of LY294002 on chemosensitivity of glioma cells. −/−, no addition; −/1 mcM VP16, U87MG glioma cells exposed to 1 mcM VP16 only; −/5 mcM VP16, cells exposed to 5 mcM VP16 only; LY/1 mcMVP16, cells exposed to 10 uM LY294002+1 mcM VP16; LY/5 mcM VP16, cells exposed to 10 uM LY294002+5 mcM VP16. Cells were incubated for 48 hours with above components prior to MTT analysis for viable cell numbers. Bars are standard deviation of mean observation.
Figure 19:
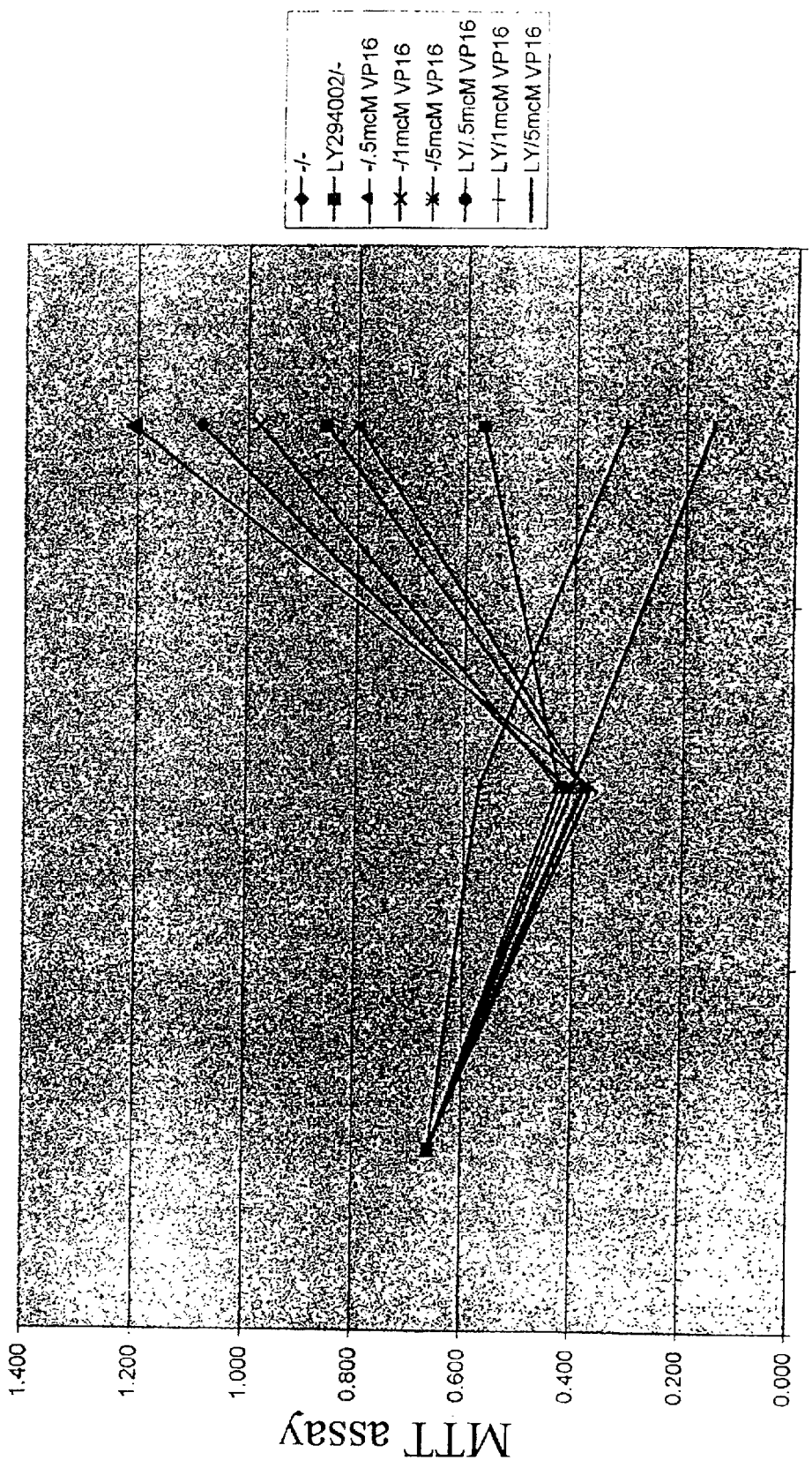
FIG. 19 is a graph showing the kinetic effect of LY294002 on Etoposide Chemosensitivity. −/−, no addition; LY294002/−, U87MG cells exposed to 10 uM LY294002 alone; −/0.5 mcM VP16, cells exposed to 0.5 mcM VP16 alone; −/1 mcM VP16, cells exposed to 1 mcM VP16 alone; −/5 mcM VP16, cells exposed to 5 mcM VP16 alone; LY/0.5 mcM VP16, cells exposed to 10 uM LY294002+0.5 mcM VP16; LY/1 mcM VP16, cells exposed to 10 uM LY294002+1 mcM VP16; LY/5 mcM VP16, cells exposed to 10 uM LY294002+5 mcM VP16. Cells were assayed by MTT at different times after addition of LY294002 and/or VP16 as shown.

The data set forth in this example implicate a role for PTEN in chemo- and radiosensitivity which influences tumor-induced angiogenesis and p53 tumor suppressor activity. Since PTEN is mutated or deleted in 50% of all glioblastoma, we assessed whether such cells are rendered sensitive to chemotherapy upon stable introduction of wild-type PTEN. U87MG glioblastoma cells, null for PTEN, or glioblastoma cells stably expressing catalytically inactive PTEN (R130M cells), required 4.7 $\mu$M of etoposide to achieve a 50% cell kill. Glioblastoma cells engineered to stably express wild-type PTEN were sensitized requiring 0.047 $\mu$M of etoposide to achieve a 50% cell kill, a 100-fold increase in sensitivity. See FIGS. 18 and 19. Compensation for the absence of PTEN in the parental line of glioblastoma was achieved by treatment of the cells with LY294002. This agent rendered the parental, PTEN-null cells as sensitive to etoposide as cells overexpressing PTEN. These observations show that PTEN and inhibitors of PI 3-kinase sensitize cancers to chemotherapy by blockade of PI 3-kinase/Akt survival signaling, thereby permitting the p53 tumor suppressor to transmit its death signal.

The following protocols are provided to facilitate the practice of Example VI.

Materials.

The D0p1 antibody to p53 was from Santa Cruz Biotechnology.

Cell Culture, Treatments, and Transfections.

U87MG cells, breast adenocarcinomas, MCF-7 cells, T47D breast ductal carcinoma cells, 293T human embryonic kidney cells transformed with adenovirus, and H1299 non-small lung carcinoma cells were cultured in DMEM supplemented with 10% fetal bovine serum at 37° C. under 5% $CO_2$. Stable clones of U87MG and U373MG glioma cells were generated using retroviral vectors pBABEpuro to express wild type and mutants of PTEN.

The MDM2 promoter with and without p53 response elements was operably linked to a nucleic acid encoding luciferase as described in Example IV. Luciferase assays were conducted twenty-four hours after transient transfection using the luciferase assay system and the galacto-light kit to assay β-gal activity.

MTT Assays.

Cells were seeded (6000/well) into a 96 well plate. Twenty-four hours later the growth medium was changed to 1% serum and other reagents were added as described. Treatments proceeded for 24–72 h. At each time point the MTT assay was performed. MTT (10 ul of a 5 mg/ml stock solution dissolved in RPMI medium) is added to each well of cultures 4 hours before quantitation of viable cell number by measuring absorbance in each well at 650 nm with a microplate reader (Molecular Devises,)

Agents added to cell LY294002 alone or in combination with etoposide. In addition, comparison was made between U87MG cells null for PTEN and reconstituted with PTEN protein. The absorbance of each well was measured at 570 nM with a microplate reader. The amount of absorbance is a reflection of mitochondrial activity of cells and hence is a method for the quantitation of viable cell numbers in multiple replicates.

Effect of PTEN Expression on Radiosensitivity.

To determine the role of PI-3 kinase pathways and PTEN in control of radiation sensitivity, U87MG reconstituted with wild type or mutant (G129R) forms of PTEN under constitutive or muristirone induced conditions were exposed in vitro to a gamma irradiation source of 12 Gy, 20Gy, 30Gy, 40Gy, 50Gy at 1.2Gy per minute as a single dose.

Cells were then washed gently and plated in tissue culture 96 well plate and at different time intervals after radiation exposure viable cell numbers were determined using MTT assay. An IC50 was established for cells expressing PTEN or treated with 5–10 uM LY294002. The results are similar to those observed with etoposide sensitivity in that PTEN reconstitution or LY294002 dramatically increased the radiation sensitivity of this p53 wild type tumor in vitro. Evaluation in vivo showed similar results as described for our experiments for antiangiogenic and antimetastatic effect of LY294002 or PTEN reconstitution.

The data reveal that the induction of p53 associated with PTEN was operative in the induction of a radiosensitive state.

The clones utilized in this example express physiologic levels of PTEN thereby more closely approximating biological reconstitution of PTEN rather than overexpression of the protein. In the studies described in the prior art and the previous examples, PTEN is overexpressed and generates cells which are growth arrested by virtue of excess levels of PTEN. PTEN expression was assessed in the present U373MG clones by Western blot and found to be equal to or less than levels of PTEN protein measured in whole brain lysates or cultivated human primary astrocytes. Ideally, assays for assessing PTEN function should be based on experimental conditions wherein PTEN expression levels accurately reflect the levels observed in normal cells. It is known that PTEN levels are closely regulated by endogenous biochemical feedback mechanisms under normal conditions thereby allowing cells to undergo regulated proliferation in response to proper physiological stimuli. Thus, PTEN functions in normal cells as a rheostat to control vital $PIP_3$ linked functions.

As demonstrated herein, PTEN activity influences the sensitivity of U87MG cells to genotoxic stress induced by the topoisomerase inhibitor, etoposide (VP16) and radiation. Exposure of U87MG cells to etoposide in the presence of PT-3 kinase inhibitor, LY294002 dramatically shifted the dose/response curve towards a more sensitive state. Similarly PTEN reconstituted tumor cells were markedly more sensitive to etoposide induced cell death and radiation. Thus, PTEN activity modulates p53 function thereby regulating and coordinating p53 levels in the cell. Accordingly, activation of PTEN and the PI-3 kinase pathway sensitizes cells to p53 mediated cell death through the control of p53 induced apoptosis.

The data reveal that LY294002 dramatically sensitizes the parental U87MG cells to the cytotoxic effect of etoposide (VP-16) as shown by MTT assay at a concentration where LY294002 has no effect on cell viability. The concentration of etoposide utilized demonstrates minimal cytotoxic activity (1 uM) while the combination of etoposide and LY294002 appears to act synergistically giving rise to enhanced cytotoxicity. There is a 5-fold increase in cytotoxicity observed in cells pretreated with the PI-3 kinase inhibitor. These results have been repeated 20 times and are highly statistically significant ($p<0.0001$) and show that LY294002 induces a chemosensitive state in this p53 wild type glioma cell line. Similar data were obtained for effect of PTEN reconstitution in this system and in other tumor cell lines. PTEN reconstitution or LY294002 induced a marked sensitivity of tumor cells to etoposide, adriamycin, cytoxan, asparaginase, vincristine, busulfan and other chemotherapeutic agents. In addition LY294002 and PTEN reconstitution induce a marked sensitivity to ionizing radiation using the same methodology.

LY294002 and PTEN reconstitution also induce a sensitivity to apoptosis induced by other environmental stress including: osmotic, endotoxic stress, nutritional stress, metabolic stress, hyperoxic, hypoxic, chemical, temperature, immunologic, other forms of electromagnetic radiation, heat shock, using the same methods for enablement. The inhibition of PTEN reduced the apoptotic response to each of these forms of cellular stress in vivo and in vitro.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for inhibiting aberrant tumor induced angiogenesis in a patient in need thereof comprising administration of a PI-3 inhibitor selected from the group consisting of LY294002 and wortmannin, said method further comprising the step of assessing inhibition of angiogenesis following administration of said inhibitor.

2. The method of claim 1, wherein said PI-3 kinase inhibitor is LY294002.

3. The method of claim 1, wherein said PI-3 kinase inhbitor is wortmannin.

* * * * *

UNITED STATES PATENT AND TRADEMARK OFFICE
CERTIFICATE OF CORRECTION

PATENT NO.     : 6,777,439 B2
DATED          : August 17, 2004
INVENTOR(S)    : Donald L. Durden It is certified that error appears in the above-identified patent and that said Letters Patent is hereby corrected as shown below:

Title page,
Item [73], Assignee, should read -- Indiana University Research and Technology Corporation --.

Signed and Sealed this

Thirtieth Day of August, 2005

JON W. DUDAS
*Director of the United States Patent and Trademark Office*

SEQUENCE LISTING

<160> NUMBER OF SEQ ID NOS: 23

<210> SEQ ID NO 1
<211> LENGTH: 1260
<212> TYPE: DNA
<213> ORGANISM: Homo sapiens

<400> SEQUENCE: 1

```
cttctgccat ctctctcctc cttttcttc agccacaggc tcccagacat gacagccatc      60
atcaaagaga tcgttagcag aaacaaaagg agatatcaag aggatggatt cgacttagac     120
ttgacctata tttatccaaa tattattgct atgggatttc ctgcagaaag acttgaaggt     180
gtatacagga acaatattga tgatgtagta aggttttgg attcaaagca taaaaaccat     240
tacaagatat acaatctatg tgctgagaga cattatgaca ccgccaaatt taactgcaga    300
gttgcacagt atccttttga agaccataac ccaccacagc tagaacttat caaacccttc     360
tgtgaagatc ttgaccaatg gctaagtgaa gatgacaatc atgttgcagc aattcactgt     420
aaagctggaa agggacggac tggtgtaatg atttgtgcat atttattgca tcggggcaaa     480
tttttaaagg cacaagaggc cctagatttt tatggggaag taaggaccag agacaaaaag     540
ggagtcacaa ttcccagtca gaggcgctat gtatattatt atagctacct gctaaaaaat     600
cacctggatt acagaccgt ggcactgctg tttcacaaga tgatgtttga aactattcca     660
atgttcagtg gcggaacttg caatcctcag tttgtggtct gccagctaaa ggtgaagata     720
tattcctcca attcaggacc cacgcggcgg gaggacaagt tcatgtactt tgagttccct     780
cagccattgc ctgtgtgtgg tgatatcaaa gtagagttct tccacaaaca gaacaagatg    840
```

-continued

```
ctcaaaaagg acaaatgtt tcacttttgg gtaaatacgt tcttcatacc aggaccagag      900
gaaacctcag aaaagtgga aatggaagt ctttgtgatc aggaaatcga tagcatttgc       960
agtatagagc gtgcagataa tgacaaggag tatcttgtac tcaccctaac aaaaaacgat    1020
cttgacaaag caaacaaaga caaggccaac cgatacttct ctccaaattt taaggtgaaa    1080
ctatacttta caaaaacagt agaggagcca tcaaatccag aggctagcag ttcaacttct    1140
gtgactccag atgttagtga caatgaacct gatcattata gatattctga caccactgac    1200
tctgatccag agaatgaacc ttttgatgaa gatcagcatt cacaaattac aaaagtctga    1260
```

<210> SEQ ID NO 2
<211> LENGTH: 403
<212> TYPE: PRT
<213> ORGANISM: Homo sapiens

<400> SEQUENCE: 2

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300
```

-continued

```
Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
            325                 330                 335

Phe Ser Pro Asn Phe Lys Val Lys Leu Tyr Phe Thr Lys Thr Val Glu
            340                 345                 350

Glu Pro Ser Asn Pro Gly Ala Ser Ser Thr Ser Val Thr Pro Asp
            355                 360                 365

Val Ser Asp Asn Glu Pro Asp His Tyr Arg Tyr Ser Asp Thr Thr Asp
        370                 375                 380

Ser Asp Pro Glu Asn Glu Pro Phe Asp Glu Asp Gln His Ser Gln Ile
385                 390                 395                 400

Thr Lys Val
```

<210> SEQ ID NO 3
<211> LENGTH: 9
<212> TYPE: PRT
<213> ORGANISM: Homo sapiens

<400> SEQUENCE: 3

```
Asp Leu Asp Leu Thr Tyr Ile Tyr Pro
1               5
```

<210> SEQ ID NO 4
<211> LENGTH: 4
<212> TYPE: PRT
<213> ORGANISM: Homo sapiens
<220> FEATURE:
<221> NAME/KEY: misc_feature
<222> LOCATION: (2)...(3)
<223> OTHER INFORMATION: Xaa = Any amino acid

<400> SEQUENCE: 4

```
Tyr Xaa Xaa Pro
1
```

<210> SEQ ID NO 5
<211> LENGTH: 5
<212> TYPE: PRT
<213> ORGANISM: Homo sapiens

<400> SEQUENCE: 5

```
Tyr Phe Ser Pro Asn
1               5
```

<210> SEQ ID NO 6
<211> LENGTH: 6
<212> TYPE: PRT
<213> ORGANISM: Homo sapiens

<400> SEQUENCE: 6

```
Tyr Leu Val Leu Thr Leu
1               5
```

<210> SEQ ID NO 7
<211> LENGTH: 4
<212> TYPE: PRT
<213> ORGANISM: Homo sapiens

<400> SEQUENCE: 7

```
Tyr Ser Tyr Leu
1
```

```
<210> SEQ ID NO 8
<211> LENGTH: 7
<212> TYPE: PRT
<213> ORGANISM: Homo sapiens

<400> SEQUENCE: 8

Tyr Arg Asn Asn Ile Asp Asp
1               5

<210> SEQ ID NO 9
<211> LENGTH: 8
<212> TYPE: PRT
<213> ORGANISM: Homo sapiens

<400> SEQUENCE: 9

His Cys Lys Ala Gly Lys Gly Arg
1               5

<210> SEQ ID NO 10
<211> LENGTH: 6
<212> TYPE: PRT
<213> ORGANISM: Homo sapiens

<400> SEQUENCE: 10

Asp His Asn Pro Pro Gln
1               5

<210> SEQ ID NO 11
<211> LENGTH: 9
<212> TYPE: PRT
<213> ORGANISM: Homo sapiens

<400> SEQUENCE: 11

His Phe Trp Val Asn Thr Phe Phe Ile
1               5

<210> SEQ ID NO 12
<211> LENGTH: 13
<212> TYPE: PRT
<213> ORGANISM: Homo sapiens

<400> SEQUENCE: 12

Thr Leu Thr Lys Asn Asp Leu Asp Phe Thr Lys Thr Val
1               5                   10

<210> SEQ ID NO 13
<211> LENGTH: 12
<212> TYPE: PRT
<213> ORGANISM: Homo sapiens

<400> SEQUENCE: 13

Gly Asp Ile Lys Val Glu Phe Phe Thr Lys Thr Val
1               5                   10

<210> SEQ ID NO 14
<211> LENGTH: 14
<212> TYPE: PRT
<213> ORGANISM: Homo sapiens

<400> SEQUENCE: 14

Asp Lys Ala Asn Lys Asp Lys Ala Asn Phe Thr Lys Thr Val
1               5                   10
```

```
<210> SEQ ID NO 15
<211> LENGTH: 19
<212> TYPE: PRT
<213> ORGANISM: Homo sapiens

<400> SEQUENCE: 15

Lys Gly Val Thr Ile Pro Ser Gln Arg Arg Tyr Val Tyr Tyr Ser
1               5                   10                  15

Tyr Leu Leu

<210> SEQ ID NO 16
<211> LENGTH: 8
<212> TYPE: PRT
<213> ORGANISM: Homo sapiens

<400> SEQUENCE: 16

Arg Tyr Ser Asp Thr Thr Asp Ser
1               5

<210> SEQ ID NO 17
<211> LENGTH: 11
<212> TYPE: PRT
<213> ORGANISM: Homo sapiens

<400> SEQUENCE: 17

Lys Gly Val Thr Ile Pro Ser Gln Arg Arg Tyr
1               5                   10

<210> SEQ ID NO 18
<211> LENGTH: 7
<212> TYPE: PRT
<213> ORGANISM: Homo sapiens

<400> SEQUENCE: 18

His Thr Gln Ile Thr Lys Val
1               5

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
gggtccacat gacagccatc atcaaagag                              29

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
ggtctagatc agactttgt aatttgtga                               29

<210> SEQ ID NO 21
<211> LENGTH: 4
<212> TYPE: PRT
<213> ORGANISM: Homo sapiens
<220> FEATURE:
<221> NAME/KEY: misc_feature
<222> LOCATION: (2)...(3)
<223> OTHER INFORMATION: Xaa = Any amino acid
```

-continued

```
<400> SEQUENCE: 21

Tyr Xaa Xaa Met
1

<210> SEQ ID NO 22
<211> LENGTH: 8
<212> TYPE: PRT
<213> ORGANISM: Artificial Sequence
<220> FEATURE:
<221> NAME/KEY: misc_feature
<222> LOCATION: (3)...(7)
<223> OTHER INFORMATION: Xaa = any amino acid
<220> FEATURE:
<223> OTHER INFORMATION: Synthetic Sequence

<400> SEQUENCE: 22

His Cys Xaa Xaa Xaa Xaa Xaa Arg
1               5

<210> SEQ ID NO 23
<211> LENGTH: 8
<212> TYPE: PRT
<213> ORGANISM: Artificial Sequence
<220> FEATURE:
<221> NAME/KEY: misc_feature
<222> LOCATION: (3)...(6)
<223> OTHER INFORMATION: Xaa = any amino acid
<220> FEATURE:
<223> OTHER INFORMATION: Synthetic Sequence

<400> SEQUENCE: 23

His Cys Xaa Xaa Xaa Xaa Gly Arg
1               5
```